United States Patent
Stoddart et al.

(10) Patent No.: US 7,105,824 B2
(45) Date of Patent: Sep. 12, 2006

(54) HIGH RESOLUTION PHOTON EMISSION COMPUTED TOMOGRAPHIC IMAGING TOOL

(75) Inventors: Hugh A. Stoddart, Harvard, MA (US); Hugh F. Stoddart, Groton, MA (US)

(73) Assignee: NeuroLogica, Corp., Danvers, MA (US)

( * ) Notice: Subject to any disclaimer, the term of this patent is extended or adjusted under 35 U.S.C. 154(b) by 97 days.

(21) Appl. No.: 10/477,064

(22) PCT Filed: May 9, 2002

(86) PCT No.: PCT/US02/14897

§ 371 (c)(1),
(2), (4) Date: Nov. 7, 2003

(87) PCT Pub. No.: WO02/089660

PCT Pub. Date: Nov. 14, 2002

(65) Prior Publication Data

US 2004/0144925 A1    Jul. 29, 2004

(51) Int. Cl.
*G01T 1/166* (2006.01)

(52) U.S. Cl. ............... 250/363.04; 250/362; 250/363.1

(58) Field of Classification Search ........... 250/363.03, 250/363.04, 363.05, 363.1, 370.1, 370.09, 250/362; 378/4

See application file for complete search history.

(56) References Cited

U.S. PATENT DOCUMENTS

| | | | | |
|---|---|---|---|---|
| 4,209,700 A | | 6/1980 | Stoddart | ..................... 250/363 |
| 4,677,299 A | * | 6/1987 | Wong | ..................... 250/363.03 |
| 4,920,491 A | | 4/1990 | Eberhard et al. | ...... 364/413.19 |
| 5,032,728 A | * | 7/1991 | Chang et al. | .......... 250/363.04 |
| 5,338,936 A | * | 8/1994 | Gullberg et al. | ....... 250/363.04 |
| 5,672,877 A | * | 9/1997 | Liebig et al. | .......... 250/363.04 |
| 5,821,541 A | * | 10/1998 | Tumer | ................... 250/370.09 |
| 6,040,580 A | * | 3/2000 | Watson et al. | ......... 250/363.03 |
| 6,175,116 B1 | * | 1/2001 | Gagnon et al. | ......... 250/363.03 |
| 6,303,935 B1 | * | 10/2001 | Engdahl et al. | ......... 250/363.03 |
| 6,310,968 B1 | | 10/2001 | Hawkins et al. | ............. 382/131 |
| 6,455,856 B1 | * | 9/2002 | Gagnon | ..................... 250/366 |
| 6,504,157 B1 | * | 1/2003 | Juhi | ..................... 250/363.04 |
| 2001/0002699 A1 | | 6/2001 | Such et al. | .................. 250/367 |

\* cited by examiner

*Primary Examiner*—David Porta
*Assistant Examiner*—Faye Boosalis
(74) *Attorney, Agent, or Firm*—Pandiscio & Pandiscio

(57) ABSTRACT

An brain scanning apparatus having a scanner device and a host computer. The scanner radiation detectors detect radiation emitted from a desired portion, or slice, of a brain source. The scanner device contains microprocessors and code which control the movement of the radiation detectors and performs the data acquisition over a number of slices and transmits this data to the host computer. The host computer initiates a scan by sending desired setup parameters to the scanner device and instructing the scanner to begin collecting data. During the scan, acquired data is sent to the host computer and spooled to a hard disk. The computer can be instructed to perform a slice by slice reconstruction of the source brain while the scan is taking place in order to produce a 2-dimensional reconstruction of the mapped brain. A complete 3-dimensional reconstruction of all the compiled slices is performed and visually displayed after acquisition of all the required slices.

9 Claims, 15 Drawing Sheets

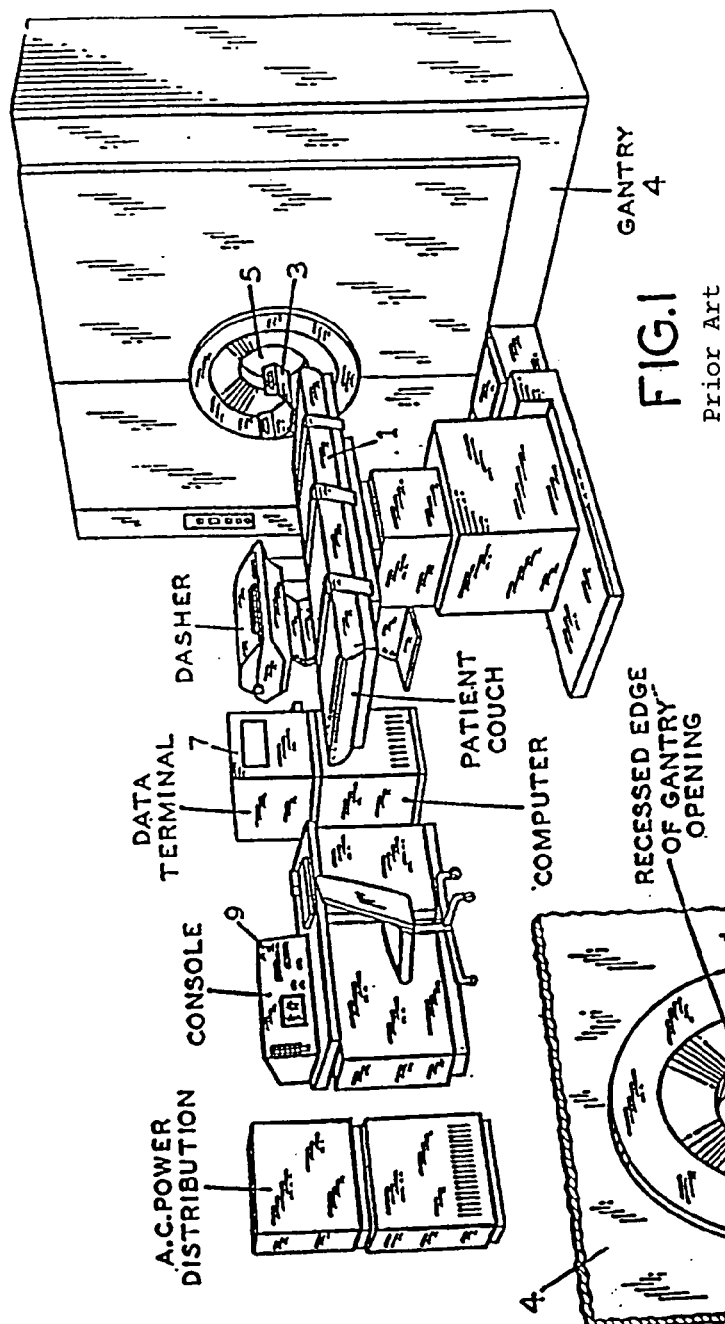
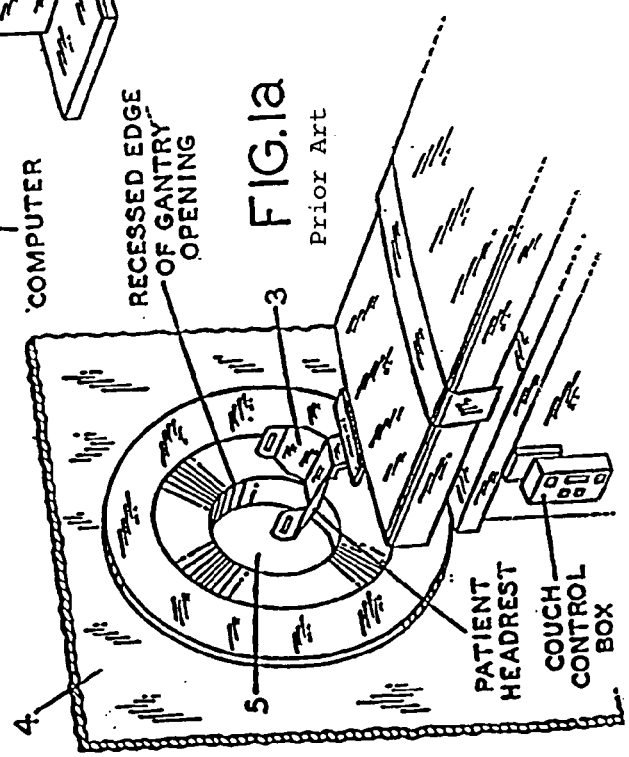
FIG.1 Prior Art
FIG.1a Prior Art

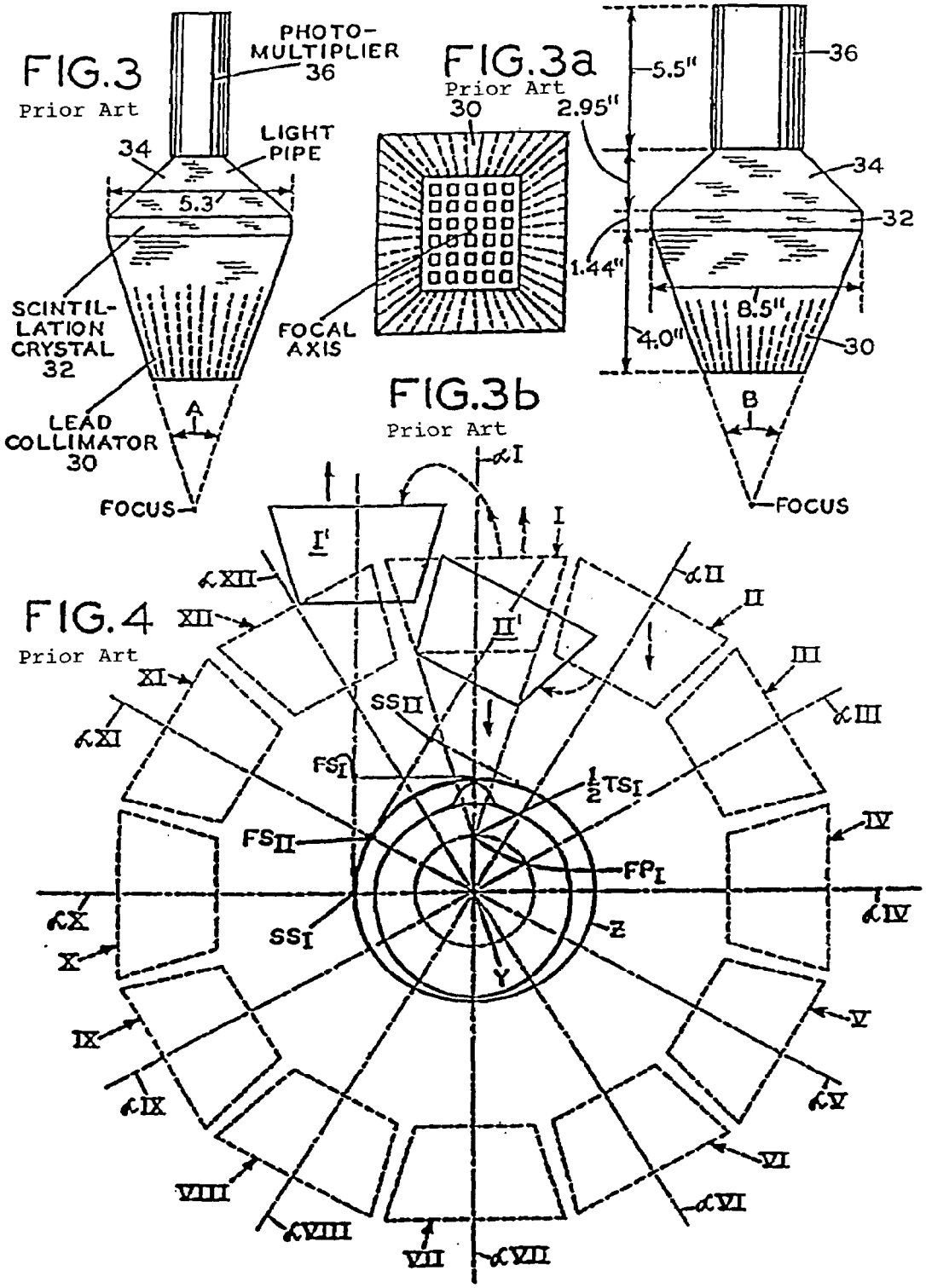

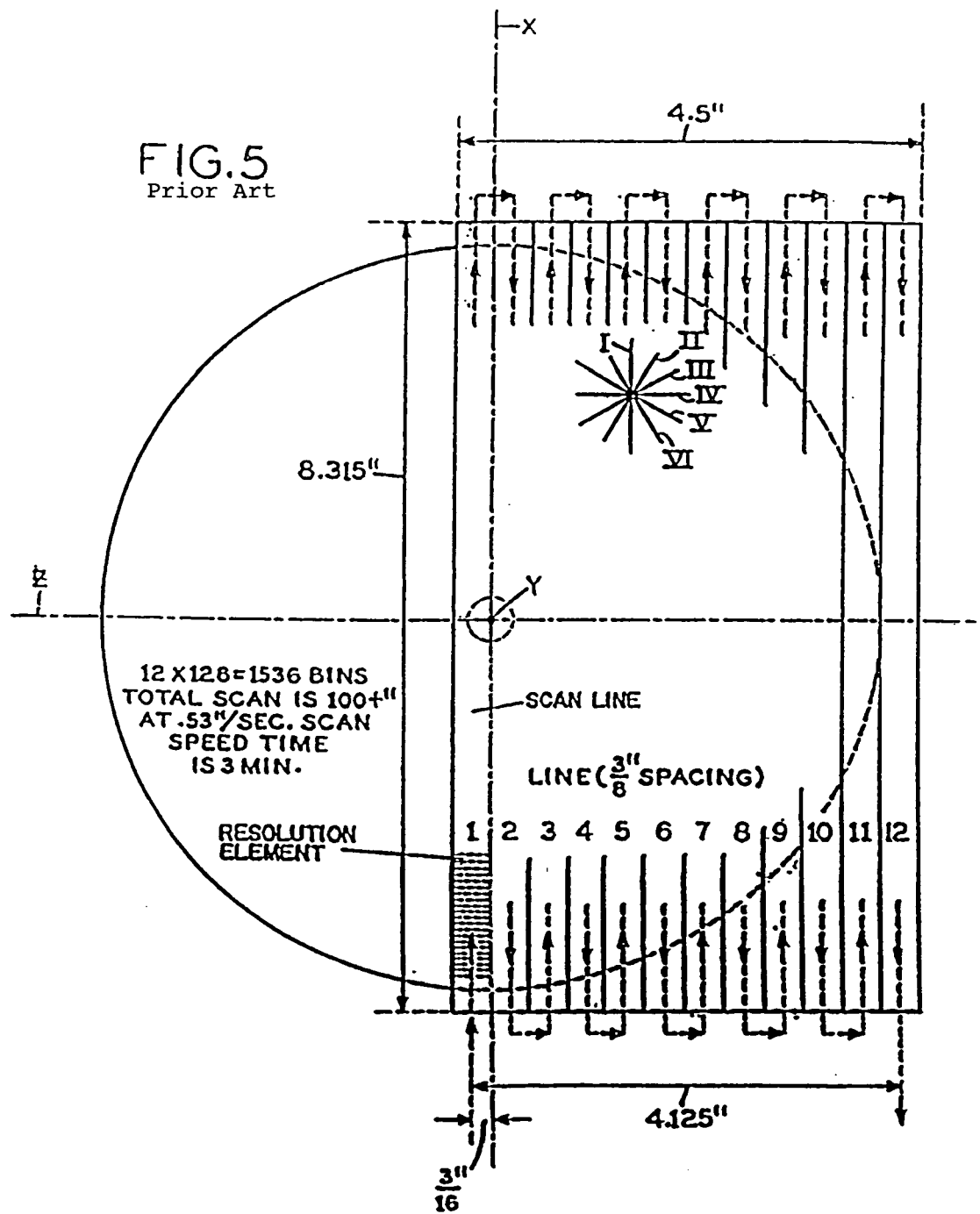

HIGH RESOLUTION PHOTON EMISSION COMPUTED TOMOGRAPHIC IMAGING TOOL

FIELD OF THE INVENTION

The present invention provides a very high resolution single-photon emission computed tomographic (SPECT) imaging tool for brain function research and brain disease diagnosis. It is intended to complement other functional imaging modalities such as positron emission tomography (PET), functional magnetic resonance imaging (fMRI), electroencephalography (EEG) and event-related potential (ERP), magnetoencephalography (MEG), and new, near-infrared optical imaging.

BACKGROUND OF THE INVENTION

In the last quarter century the use of brain imaging for the treatment and understanding of diseases and genetic flaws has grown dramatically following the introduction of Tomographic X-Ray (CT) in 1972 followed in 1982 by magnetic resonance in the gene (MRI). The reason for this growth and importance in brain imaging is that neurologists, psychotherapist, and neuro-scientists utilize and attached substantial importance to high resolution, three dimensional anatomical images of the brain. The development of functional brain imaging which seeks to map the distribution of brain activity has closely followed the development of structural imaging which maps some physical property of the brain such as tissue density. While SPECT is playing an important role in functional brain imaging, it has been limited in many applications by its low spatial resolution. The tiny structures of the brain where thinking takes place are much smaller than the resolution of the best SPECT scanners and therefore are not seen. Only in the situations where gross functional changes or small changes over a large population of subjects have occurred is SPECT useful.

U.S. Pat. No. 4,209,700 to Stoddart discloses a first generation nuclear transverse sectional brain function imager. Stoddart discloses an imaging apparatus having a transverse radio nuclide scanfield and a method for using highly focused collimators in an array surrounding the scanfield. This allows the scanner to concentrate its information gathering capability on a single cross-section of the head as opposed to the rotating gamma camera whose sensitivity is distributed over the entire volume of the head. In the situations where only part of the brain is of interest, this is a huge advantage, especially for dynamic studies where one needs to make rapid repetitive scans of the same area. The scanner is not limited to single sections. By moving the patient through the scanner, a stack of sections may be obtained which cover the entire volume of the head.

In general, the typical clinical resolution of the best SPECT rotating gamma-cameras is about 7 mm. This is inferior to both PET and fMRI which provide 5 mm and 3 mm resolution, respectively. The two avenues of improvement used to bring rotating gamma-cameras to their state-of-the-art are: 1) increasing the number of camera heads (now 3) and 2) modifying the original parallel hole collimator design to the higher performance mildly converging tapered hole designs' while increasing camera area in order to maintain a sufficiently large field-of-view (FOV). Further improvement is difficult since the cameras of 3-headed systems now totally encircle the patient with little room left for more or larger versions.

Collimators are simply blocks of lead with holes drilled through them (or cast with holes in them) to allow gamma rays to pass through which are traveling in a specific direction. The longer or narrower the holes, the more precise that direction becomes. This is good for geometrical resolution but bad for sensitivity and one needs both. Tapered holes are vastly superior than straight holes in that they provide both better geometrical resolution and sensitivity at the same time. While rotation gamma-cameras benefitted from mildly tapered holes, they cannot take advantage of highly tapered holes since the resulting FOV would not cover the entire head. The present scanning system overcomes this problem by sweeping the narrow FOV.

OBJECT AND SUMMARY OF THE INVENTION

The present invention is a major advance in the resolution of SPECT brain function imaging, surpassing PET scanners, and equaling fMRI.

The present invention utilizes a collimator with a sharp focus within the object, and steeply tapered holes that provide extremely high sensitivity-resolution characteristics. This requires that the detector be translated and moved radially-but, with sufficient numbers of detectors to provide 360 degree scanfield coverage, no rotational movement is necessary. By its nature, namely the constant size and configuration of the lead collimator throughout the scanning process, the present scanner has uniform resolution throughout the object volume (spatially invariant point spread function "PSF") and produces zero spatial distortion. Furthermore, it is immune to various gamma camera effects caused by errors in finding exact scintillation locations from weighted photomultiplier output pulses.

BRIEF DESCRIPTION OF THE DRAWING(S)

FIGS. 1 and 1A show the general arrangement of a particular embodiment of the present invention;

Figure 2:
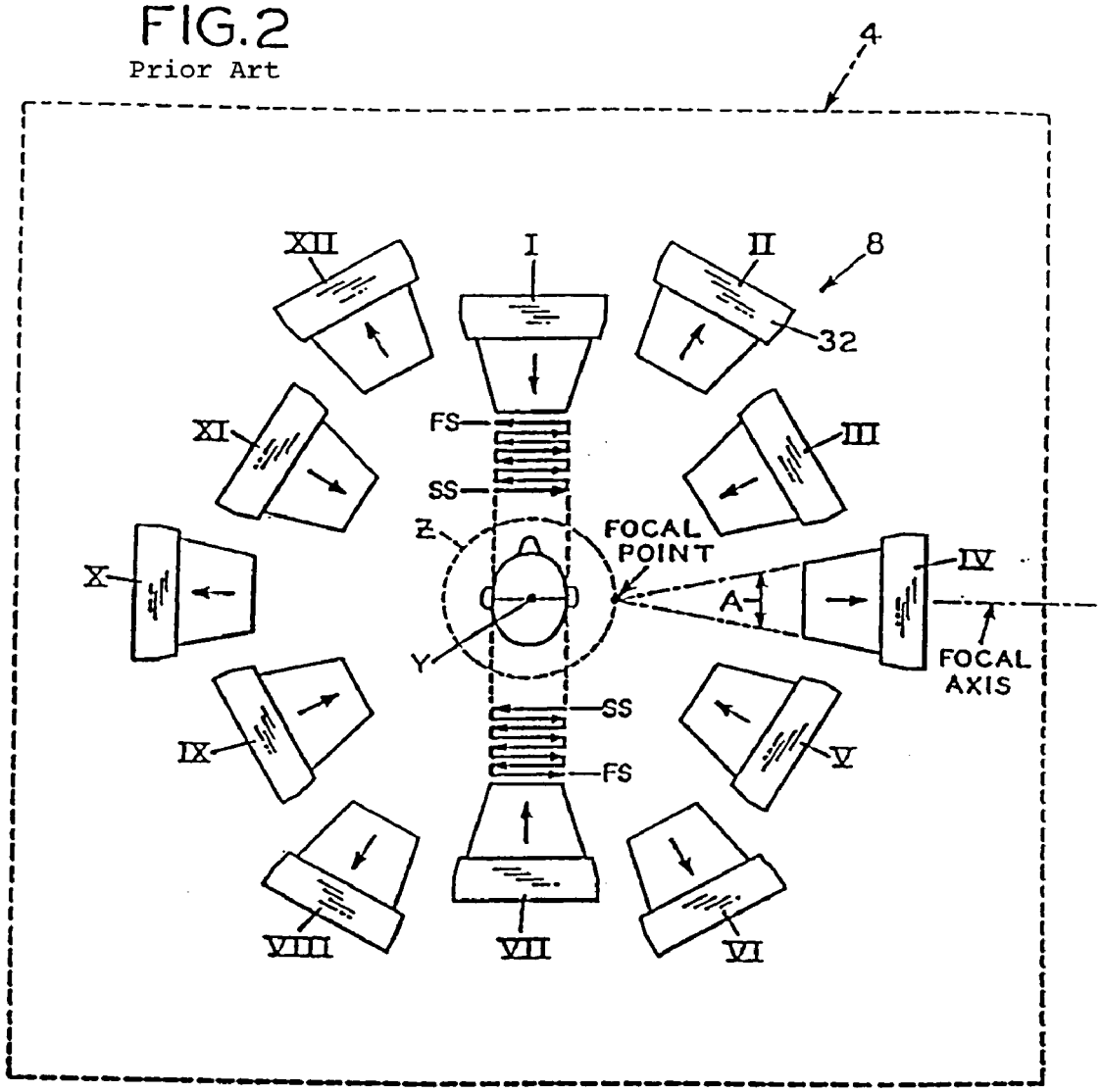
FIG. 2 shows, somewhat schematically, an imager in accordance with the present invention.
Figure 2A:
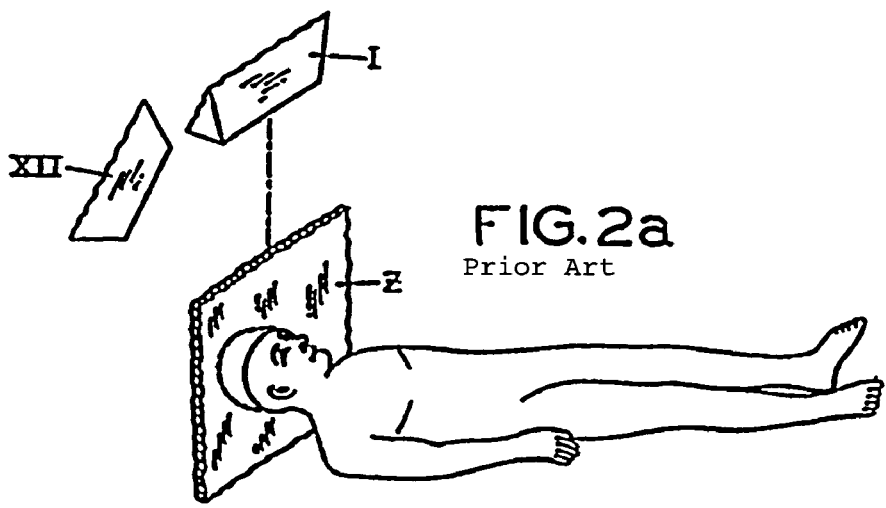
Figure 4A:
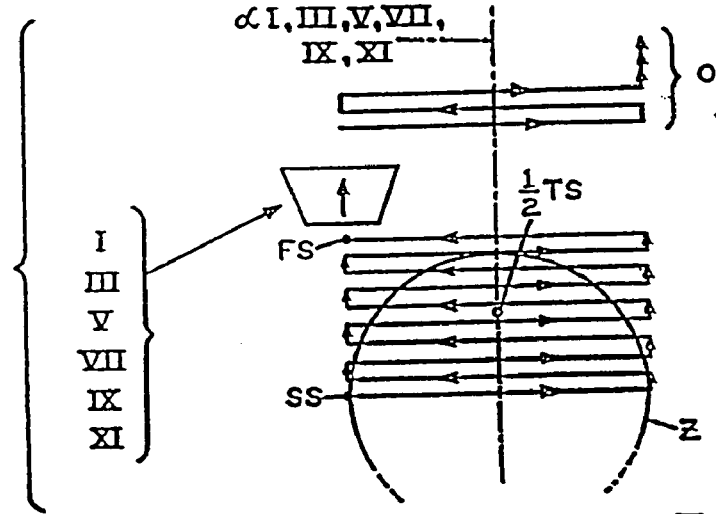
Figure 4B:
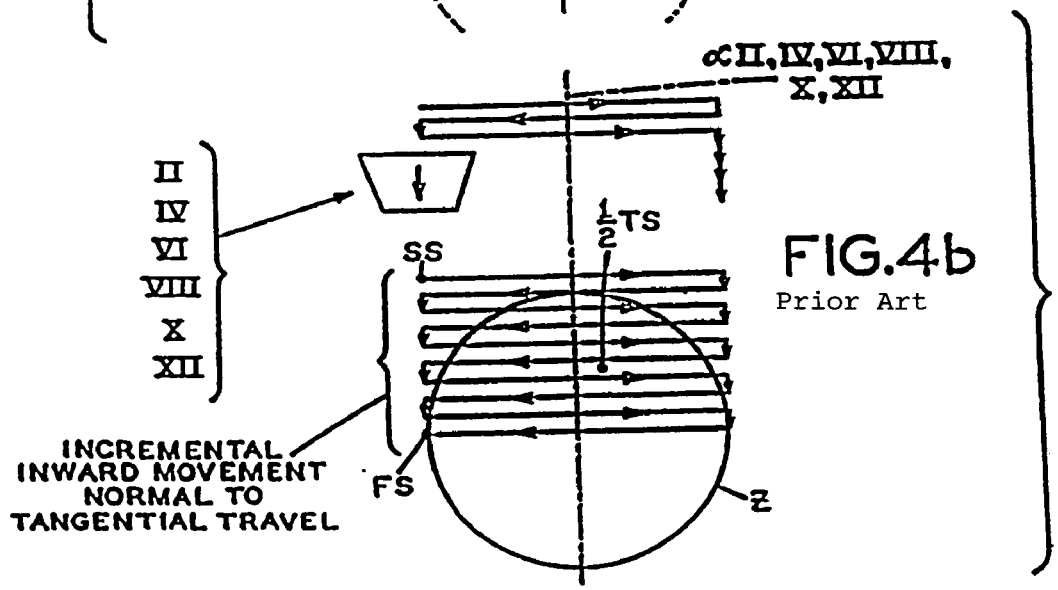
Figure 5A:
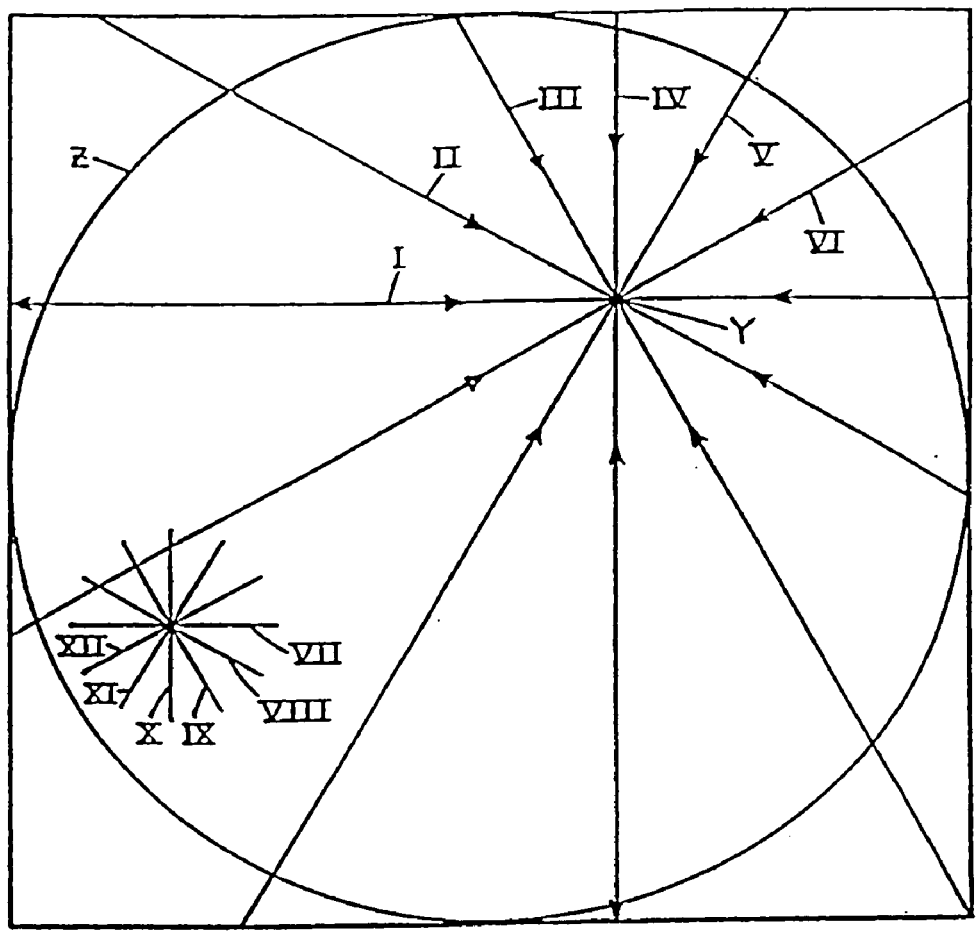
Figure 6:
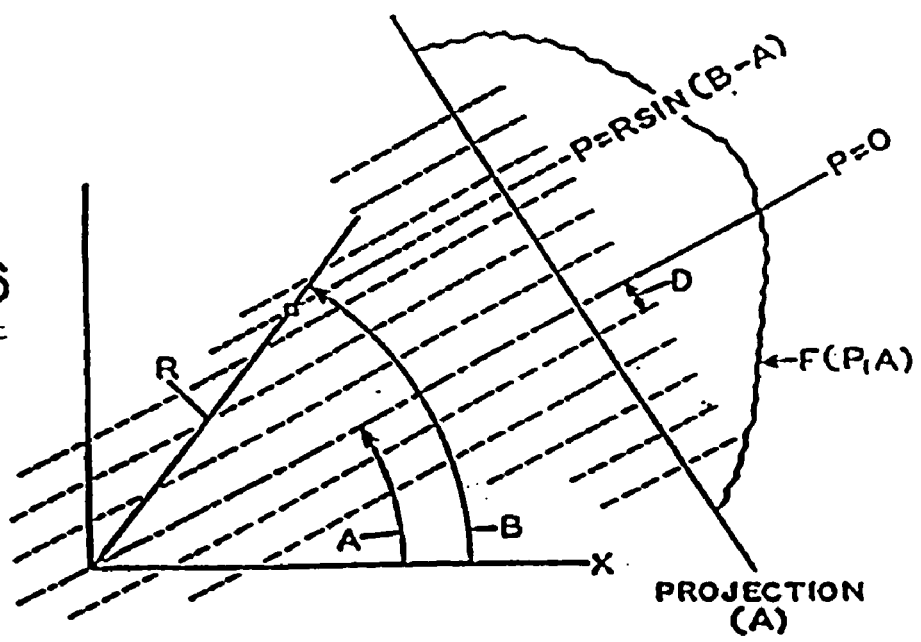
Figure 5B:
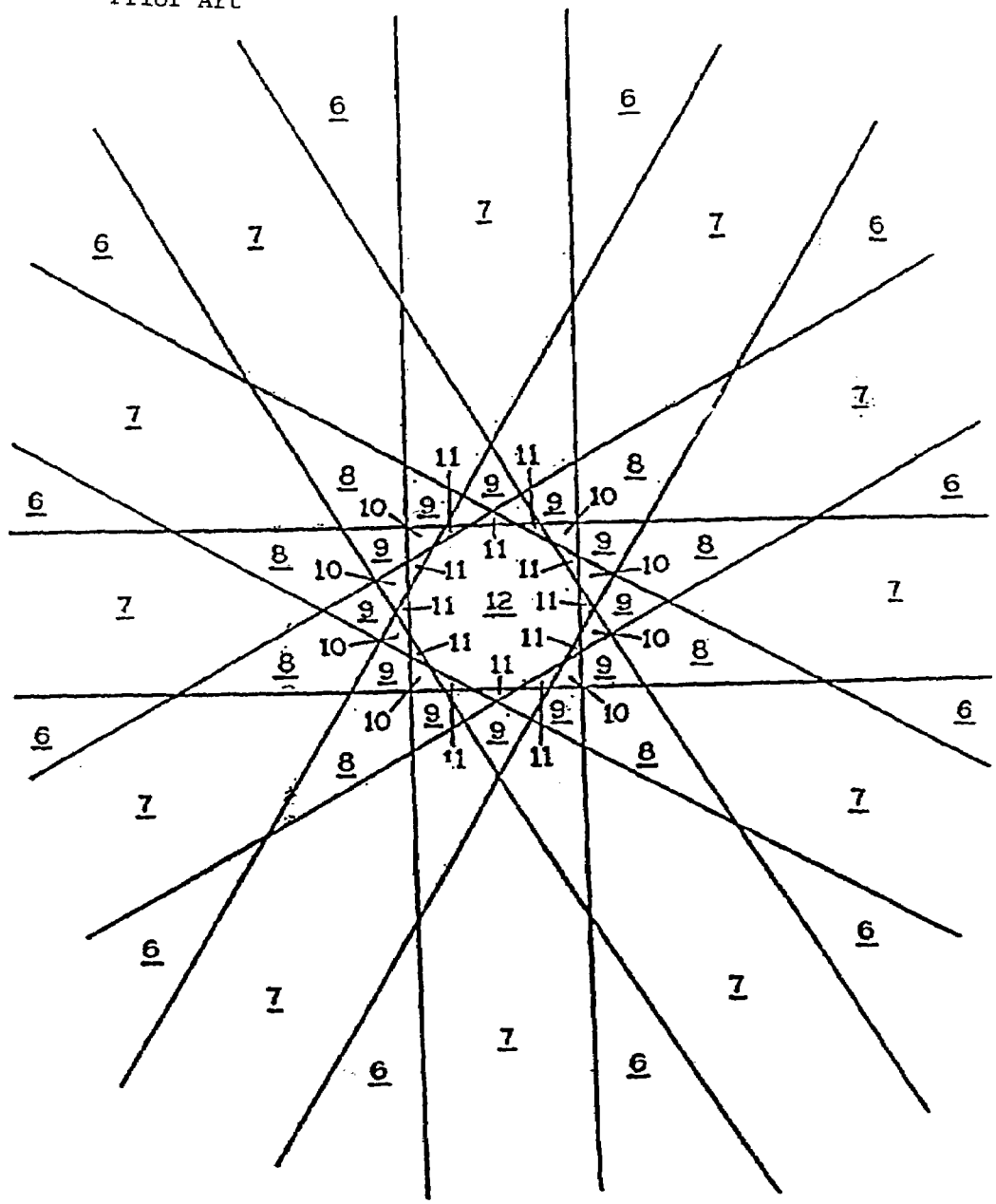
Figure 7:
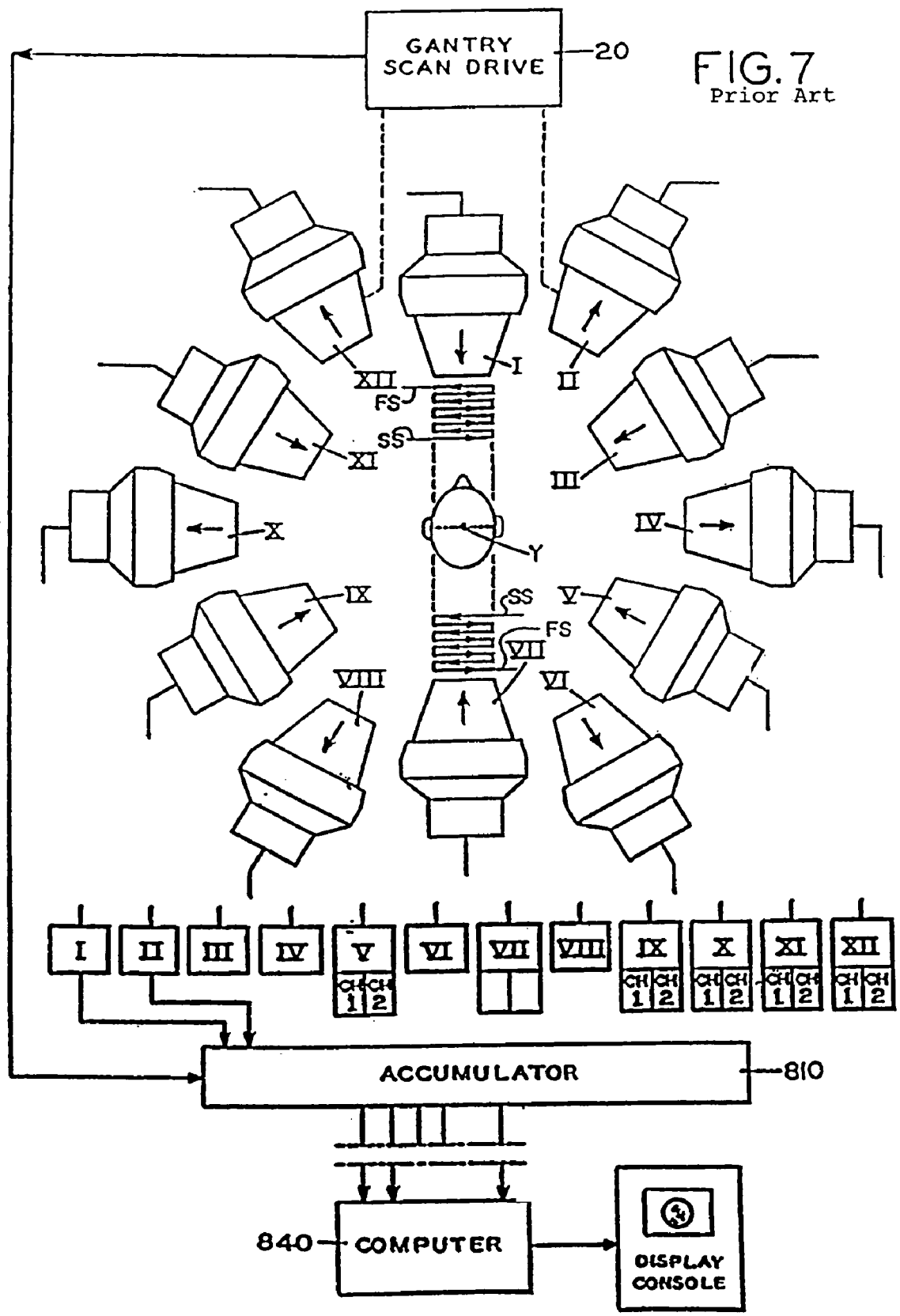
Figure 8A:
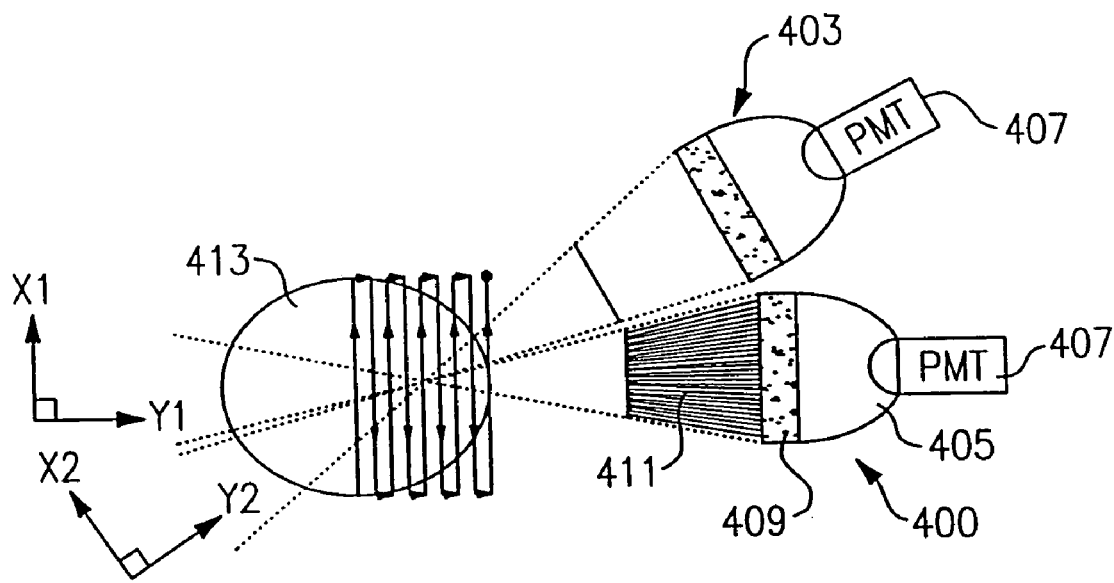
Figure 8B:
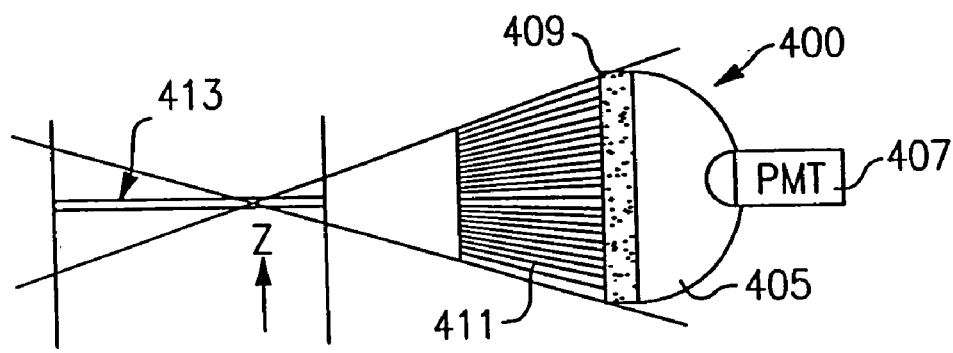
Figure 9A:
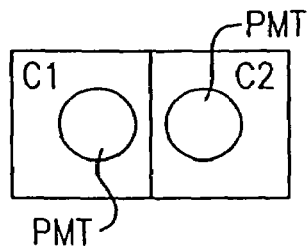
Figure 9B:
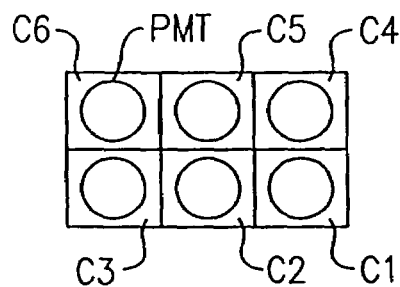
Figure 9C:
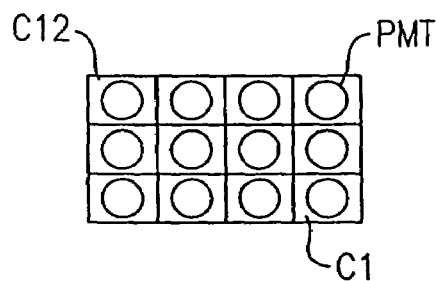
Figure 10:
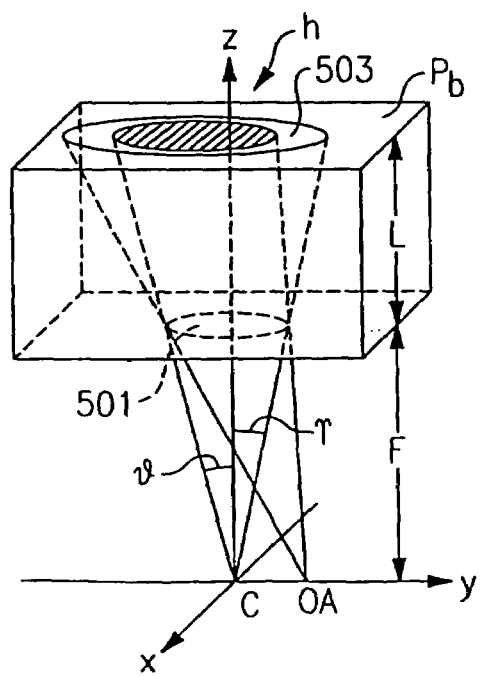
Figure 11:
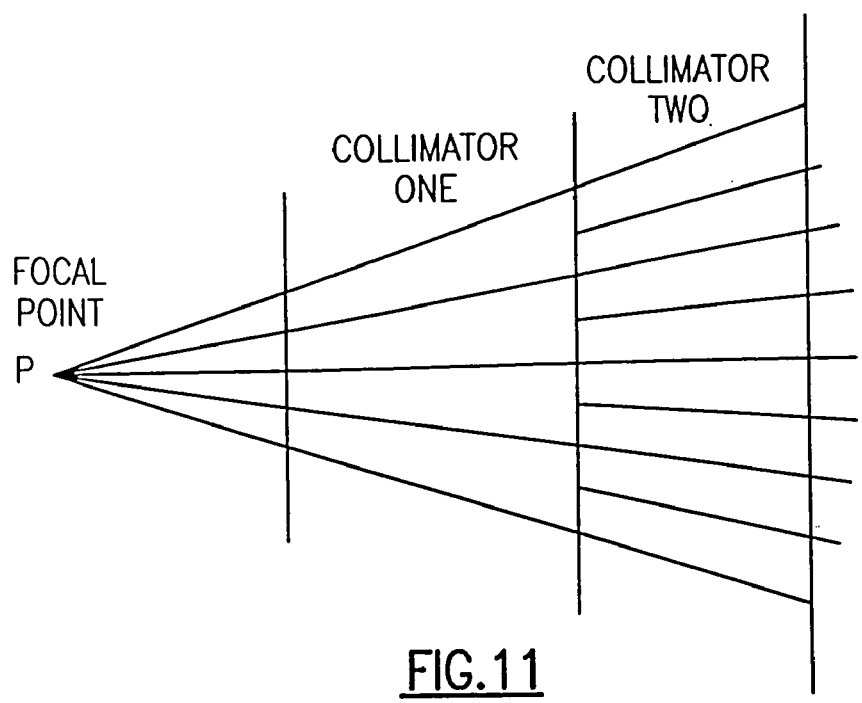
Figure 12A:
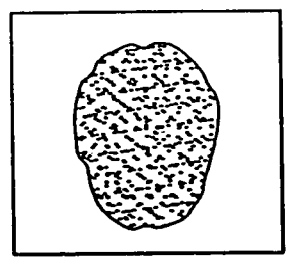
Figure 12B:
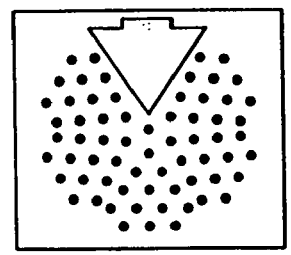
Figure 13A:
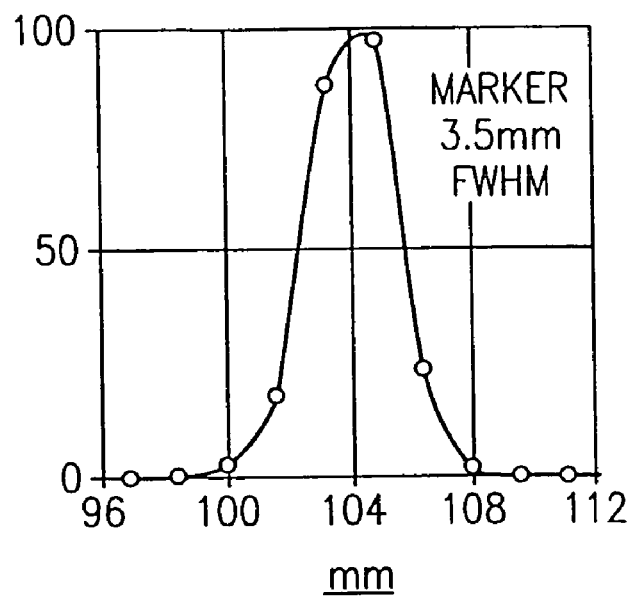
Figure 13B:
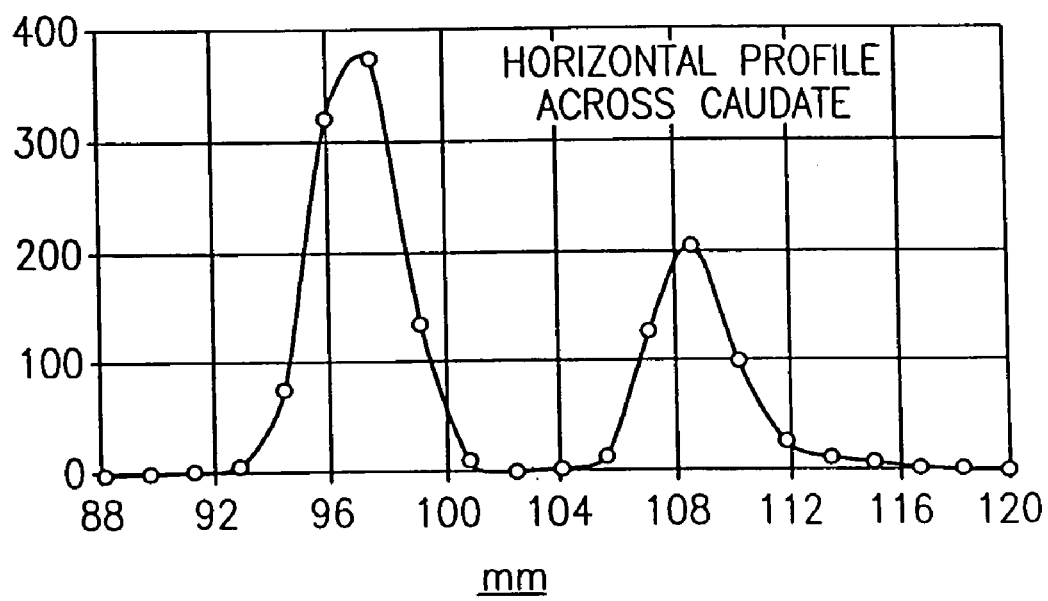
Figure 14:
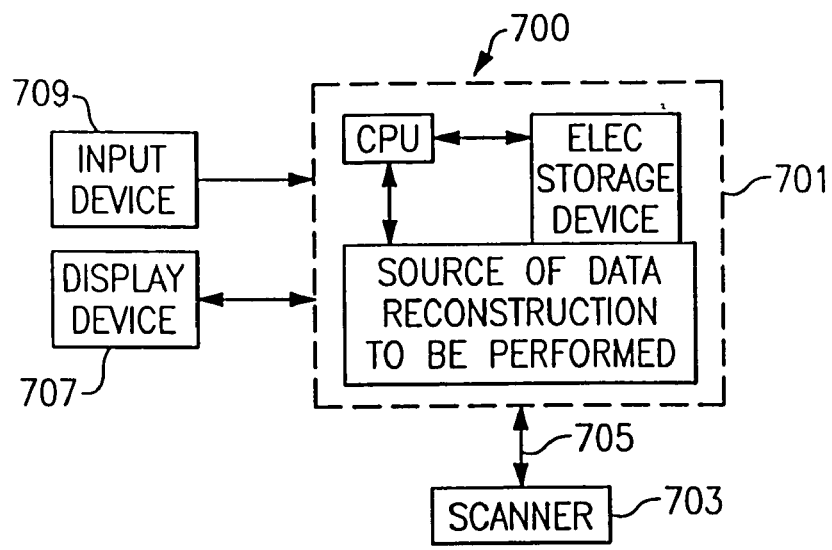
Figure 15:
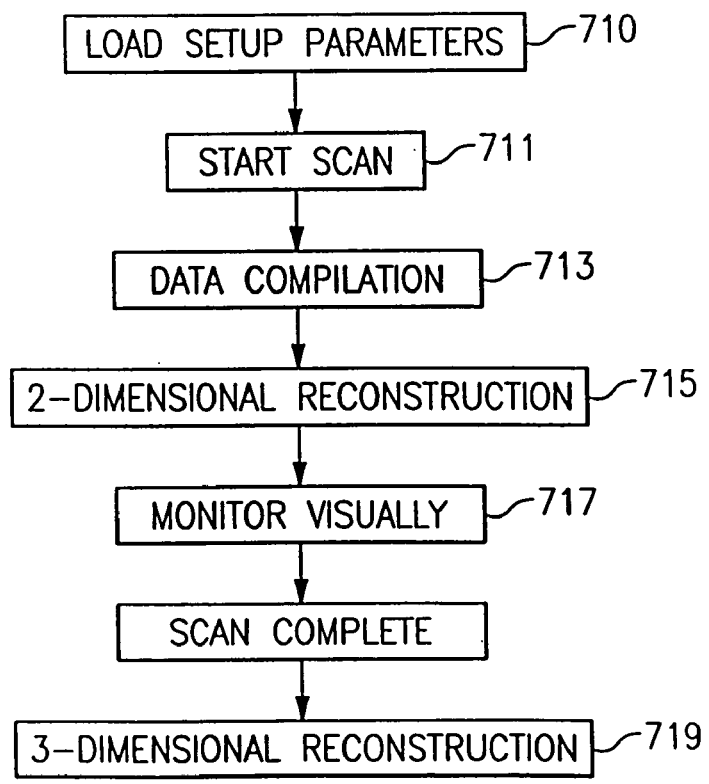
Figure 16:
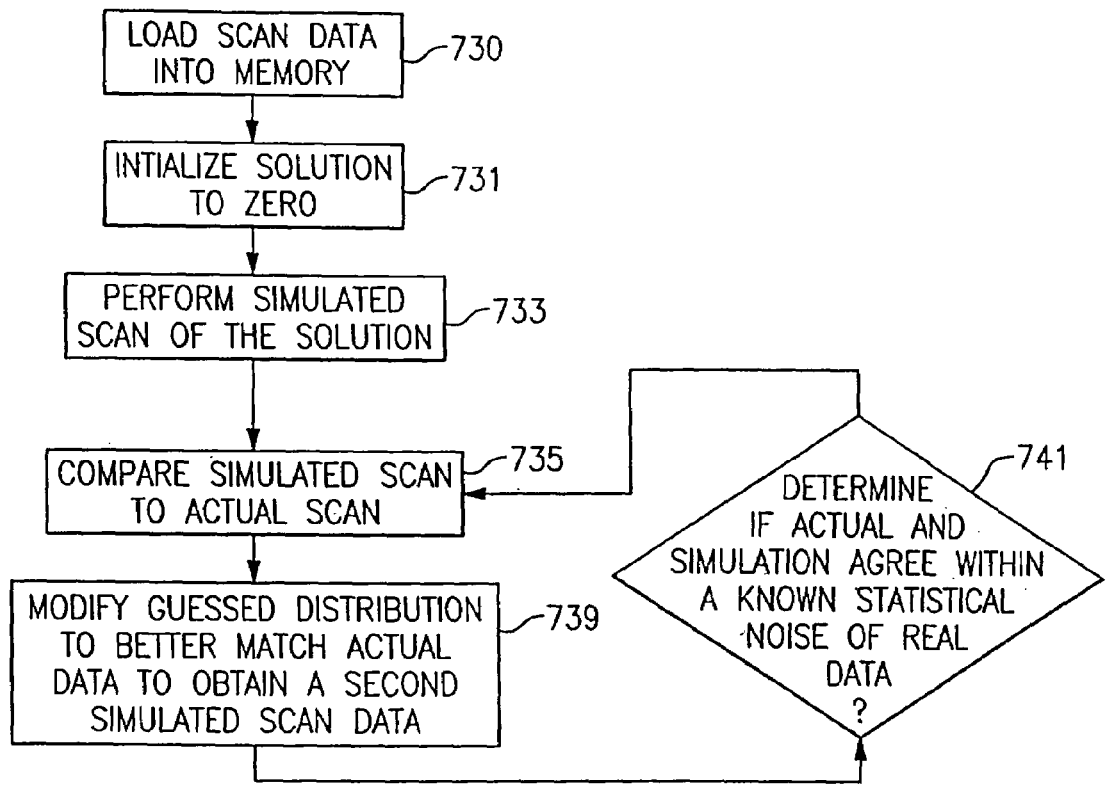
Figure 17:
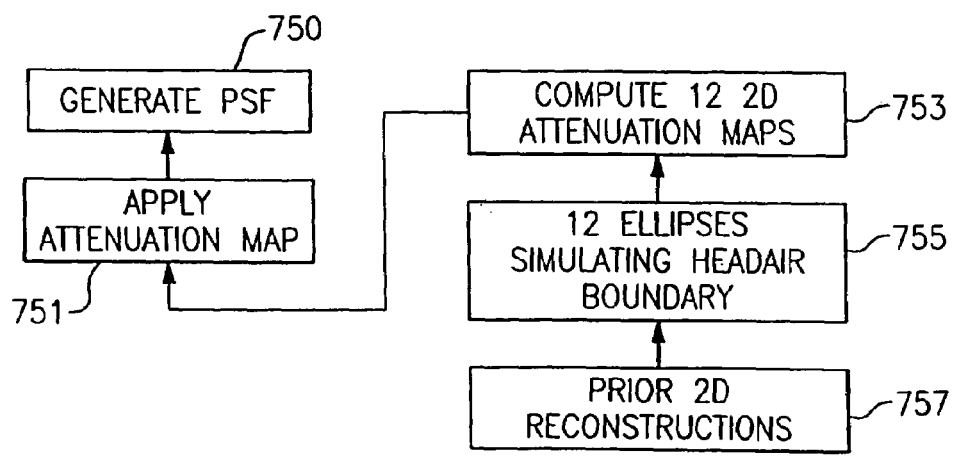
Figure 18:
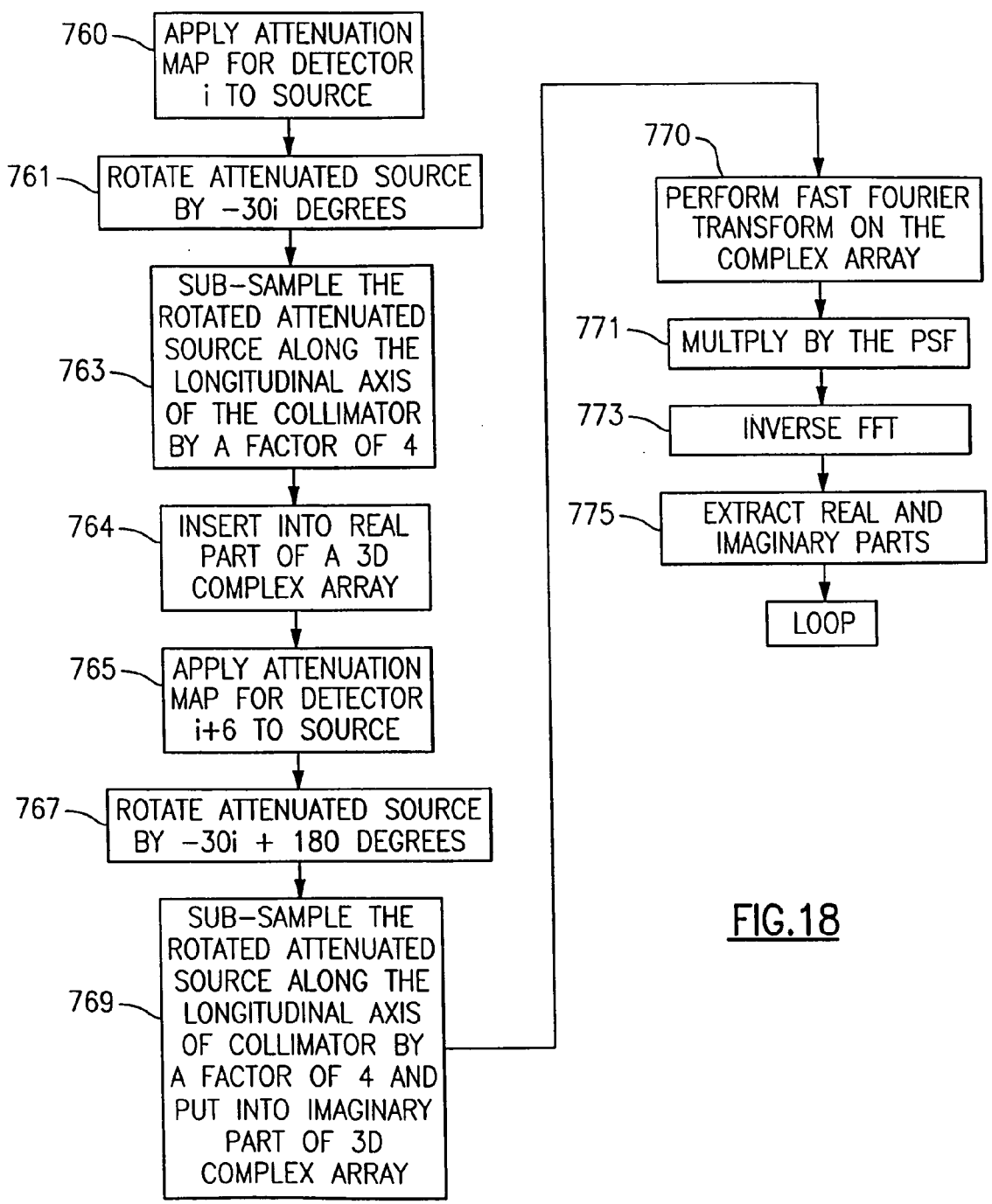

FIGS. 2A, B and C illustrate a patient in relation to the imager of the present invention;

FIGS. 3, 3A and 3B show a detector arrangement, including a highly focused collimator, for use in connection with the present invention;

FIG. 4 illustrates schematically an arrangement of highly focused collimators in accordance with the present invention and further illustrating representative relative movement of the collimators;

FIGS. 4A and 4B illustrate schematically a scanning pattern of highly focused collimators in accordance with the present invention;

FIG. 5 shows a preferred scanning pattern in accordance with the present invention;

FIGS. 5A and 5B illustrate particular representative portions of the scanning pattern of FIG. 5;

FIG. 6 is a diagram used in connection with a mathematical presentation in the specification;

FIG. 7 schematically represents a general arrangement for the imager of the present invention;

FIGS. 8A and 8B represents a simplification of the scan pattern from a horizontal cross section view and a transverse cross section of a source brain view respectively;

FIGS. 9A, 9B and 9C shows a series of 1×2, 2×3 and 3×4 arrays of scintillation crystals and associated photomultiplier tubes;

FIG. 10 is a theoretical representation of a tapering collimator;

FIG. 11 is a diagrammatic representation of a stacked first and second collimators having a focal point at a single point P;

FIGS. 12A and 12B are pictorial representations of a reconstructed and displayed image of a brain;

FIGS. 13A and 13B are graphical representations of the improved imaging process of the present invention;

FIG. 14 is a block diagram showing a general overview of the system components;

FIG. 15 is a flow diagram of the reconstruction method;

FIG. 16 is a flow diagram detailing the reconstruction algorithm;

FIG. 17 is a flow diagram of the simulation method used in the reconstruction method and;

FIG. 18 is a flow diagram of a convolution algorithm as used in the present invention.

DETAILED DESCRIPTION OF THE INVENTION

With reference to FIG. 1, a patient's couch is indicated at 1 which is provided with controls, not shown, for raising and lowering the couch 1, and for moving the headrest 3, of couch 1, in and out of the opening 5 of the gantry indicated at 4. Within gantry 4, as hereinafter more fully described, there is arranged, in a unique and novel manner, a plurality of scanning detectors, having highly focused collimators, from which electrical signals are obtained which are readily processed, e.g. by a general purpose computer, and enable a display at console 9 of a transverse section of the brain of a radionuclide administered patient, which display exhibits high sensitivity quantification and spatial resolution. The patients couch 1 is moveable in and out of the opening 5 of the gantry 4 to provide for the scanning of a plurality of transverse sections.

With reference to FIG. 2, this figure shows at 8 an essentially schematic representation of the arrangement of scanning detectors with gantry 4. Each of the detectors indicated at I to XII in FIG. 2 is of a type more fully illustrated in FIGS. 2 and 3A which show a highly focused lead collimator at 30, a scintillation crystal at 32, a light pipe at 34 and a photomultiplier tube at 36. Such an arrangement has the dimensions shown in the drawing when twelve detectors are used to suitably comprise a collimator made of antimony-bearing lead alloy containing a 22×26 array of tapered holes of rectangular cross-section. These holes are typically 0.320×0.160 in. On the face of the collimator that abuts the scintillation crystal 32, and about 60% of that size at the opposite face. All of the holes are convergent so that the axes intersect at a focus 6 inches form the collimator. The septa separating the holes are approximately 0.0010 inch thick at the crystal face. A typical design resolution of collimator 30, defined at the full width between two points that give half amplitude for a point source of radiation is 0.3 inch in the plane of the transverse section and 0.05 inch perpendicular to the slice (slice thickness).

The scintillation crystal 32 typically comprises a thallium activated sodium iodide crystal mounted within a rectangular aluminum box and sealed under a window of ultraviolet transmitting glass. The bottom wall of the aluminum housing is thin, preferably less than 0.02 inches, to minimize absorption and scattering of the incident gamma rays.

A very important feature of the present invention is that the collimator used is highly focused at a single focal point, i.e. all the holes in the collimator converge at the focal point so that the collimator includes a large solid angle from about 0.05 to 1 steradian, preferably about 0.4 steradian, for collecting radiation.

Figure 2B:
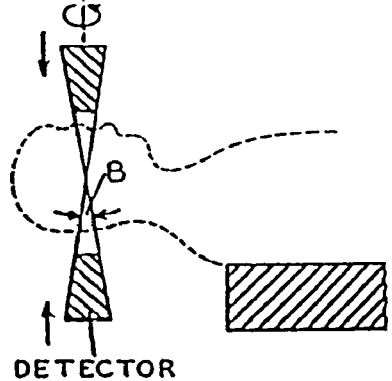
Figure 2C:
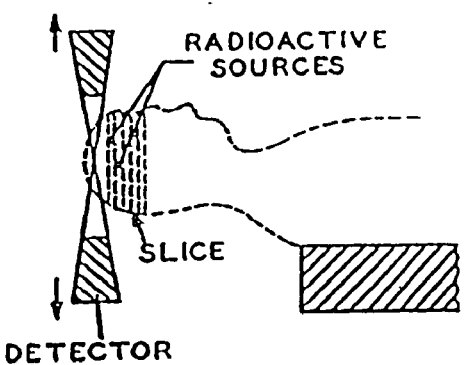

In a configuration such as illustrated schematically in FIG. 2, where twelve focused collimators are used, the angle "A" is approximately and as close as practical to 30° (360÷12), e.g. about 24° and the angle "B" shown in FIGS. 2B and 3A is approximately 38.5°. When other than twelve collimators are used, e.g., 4, 8, 10, the design for angle "A" (±6°) is obtained by dividing the number collimators into 360°. In the present invention, the focal length of the collimators (6 inches) is somewhat more than one-half the diameter of the scan field which surrounds the portion of the patients body which is scanned.

In the present invention, the preferred number of collimators is twelve to obtain high sensitivity and resolution in a short period of time, e.g., about 2 minutes per slice. The preferred range for the number of collimators is from 6 to 24 even numbers of collimators. Even umbers of collimators are preferred since they can be arranged in pairs with each collimator scanning half of the transverse section of the organ thereby minimizing effects of attenuation and scattering. With odd numbers of collimators, each collimator preferably scans the entire transverse section of the organ.

Referring again to FIG. 2, detectors I to XII are mechanically mounted and coupled to gantry 4, as hereinafter more fully described, to provide focal point scanning of a transverse section "Z" which is normal the head-to-toe axis of the patient and indicated schematically in FIG. 2A. With reference to FIG. 2, which shows exemplary distances, the position of the detectors I–XII can be considered to represent the start (or finish) of a focal point scan. The alternate pairs of opposed detectors I–VII, III–IX, V–XI, are shown in what can be called the "full in" position. The other alternate pairs of opposed detectors II–VIII, IV–X, and VI–XII, are in what can be called the "full out" position. Upon commencement of a scan, each detector I–XII moves in a straight line tangential to the scan filed Z in the same rotational sense (either clockwise or counter-clockwise angular rotation abo the "head-to-toe" axis Y of the patient) the tangential travel of each detector being the same, a full diameter, or across two adjacent quadrants of scan filed. Upon completion of each tangential travel, the "full in" detectors, I, III, V, VII, IX and XI move away from the axis Y a predetermined increment normal to the tangential travel, the "full out" detectors "II, IV etc." move toward the axis Y by the same increment and the direction of the tangential travel of all detectors is reversed. This coordinated movement of the detectors is repeated until the focal point of each detector scans at least one half of the area of the scan filed, preferably more than one-half as hereinafter described, at which time the scanning is completed and the initially "full in" detectors are in "full out" position and vice versa. It is to be noted that the region scanned by the focal point of each detectors overlaps, by an angular segment, the focal point scan of the other detectors. In the case of twelve detectors, there is a 30° segment of overlap of adjacent detectors and each scanned point in the scan field is scanned by the focal point of at least six detectors as hereinafter described.

By way of further explanation, FIG. 4 shows schematically, the detectors I–XII at their respective halfway positions for calibration. At the "½ way" position shown in FIG. 4 all of the detectors I–XII are at the same distance from axis Y and as particularly illustrated for detector I, the focal point $FP_I$ is halfway in the scan field. As the scan is completed, detector I moved out and over following the tangential and incremental motion previously described, to the position I' where the focal point scan for detector I is completed (Full Scan I). Concurrently, the same relative motion is being experienced by detectors II, V, VII, IX and XI. The relative movement of the even numbered detectors is represented by detector II. As the scan is completed, detector II moves in and over the position II' where the focal point scan for detector II is completed (Full Scan II). FIG. 4A illustrates schematically the focal point scan provided by each of the six "outward" moving detector III, etc. The scan shown is provided, for the respective detector, along the respective radial angle indicated, i.e. $a_I$, $a_{III}$–$a_{XI}$. A similar presentation is shown in FIG. 4B for the six "inward" going detectors II–XII. As is representatively illustrated in FIG. 5, any point in the transverse section Z is focal point scanned by at least one half of the total detectors, i.e., at least six in the presently considered embodiment. Because of overlaps the central region is scanned by up to 12 detectors. This overlap, which is provided by all twelve detectors in the preferred embodiment of the present invention, permits convenient equalization and normalization of the detectors. FIG. 5 shows a focal point scan for an "outward" going detector e.g. detector I and provides, for a twelve line scan, typical dimensions for scan line length (8.315 inches) spacing ⅜ inch), resolution elements (128 per line) and the like. As shown in FIG. 5, the exemplary point "R" is "focal point scanned" by the six detectors, I, II, III, IV, V and XII. FIG. 5A is based on FIG. 5 and shows the detectors which scan two arbitrarily chosen points in the scan field which are scanned by six detectors; FIG. 5B, also based on FIG. 5, shows the central region of the scan where scanning by up to twelve detectors occurs. The numbers in FIG. 5B show the number of detectors which scan the indicated region; the same type of information for any point in the scan field can be routinely determined from grids of this type in relation to the position of the detectors.

In the course of a transverse focal point scan as described above, each detector continuously receives the emitted radiation, e.g., gamma photons appearing within the included angle of the collimator and this radiation is converted into counts by the associated scintillation crystal and photomultiplier tube of each detector. Electrical signals provided by respective photomultiplier tube can be conventionally amplified, detected by pulse amplitude discrimination techniques, identified as to spatial orientation in the scan field and, in the form of digital numbers corresponding to counts and detector position, transferred to the memory of a general purpose computer. The stored information thus provided is, on account of using highly focused collimators in accordance with the present convention, readily reconstructed to provide a high sensitivity quantification and spatial location of the radioactivity in the transverse section which is focal point scanned. This is so since focusing collimators inherently sum the counts from each point, and by focal point scanning in and out as well as tangentially, the combination of collimators cover (sum) substantially 360° about each point in the transverse scan. The counts thus collected are predominately counts originating at the focal points of the collimators but also include (convolved with) some counts from "out of focus points". These unwanted counts can be removed by deconvolving the stored information with a filter function $H(r)^{-k}(K>1)$ by a relatively simple algorithm such as taking a Fourier transform of a ramp in frequency space;

for example, as described in "The Fourier Reconstruction of a Head Section"-L. A. Shepp, B. F. Logan "IEEE Transactions on Nuclear Science" vol. NS-21, June 1974. The resulting reconstructed data is then available for display showing quantified and spatially oriented radioactivity. Other known techniques can also be used to remove the unwanted counts.

The concept of using highly focused collimators for this purpose is based on the recognition that the Radon equation, can be put in a form that demonstrates that reconstruction using the counts summed (collected) over large angle sis possible.

With reference to FIG. 6

Radon:

$$G(R, B) = \frac{1}{2\pi^2} \int_{-\frac{\pi}{2}}^{+\frac{\pi}{2}} \int_{-\infty}^{\infty} \frac{\partial F(A)}{\partial P} \frac{1}{R\text{SIN}(B-A)-P} dP dA$$

$$\frac{1}{2\pi^2} \int_0^{\pi} dA \int_{\infty}^{\infty} \frac{dF(P, A)}{dP} \frac{1}{R\text{SIN}(B-A)-P} dP$$

To reconstruct a point at the origin:

$$G(o) = -\frac{1}{2\pi^2} \int_0^{\pi} dA \int_{-\infty}^{\infty} \frac{dF(P, A)}{P}$$

LET $dA=\Delta$, $Am=m\Delta A$ $M=$number of projections $(\pi/\Delta A)$. Replacing Derivative by Difference, $$G(o) = \frac{\Delta A}{2\pi^2} \sum_{m=1}^{M} \sum_{n=1}^{N} \frac{F[(n+1)D, m\Delta A] - F[nD, m\Delta A]}{\left(\frac{nD+(n=1)D}{2}\right)}$$

SINCE $\frac{\Delta A}{\pi} \sum_{m=1}^{M} F(m\Delta A) = \overline{F}()$ The average of $F()$ over all angles AND $\frac{nD+(n+1)D}{2} = \frac{D}{2}(2n+1)$ $$G(o) = -\frac{1}{2\pi} \cdot \frac{2}{D} \sum_{n=-N}^{N} \frac{\overline{F}[(n+1D] - \overline{F}(nD)}{2n+1}$$

$$-\frac{1}{D\pi} \left\{ \frac{\overline{F}(D) - \overline{F}(o)}{1}_{(n=o)} + \frac{\overline{F}(2D) - F(D)}{3}_{(n=1)} + \frac{\overline{F}(o0 - F(-D) + ...}{-1}_{(n=-1)(n=-2)(n=-2)} \right\}$$

$$\frac{1}{D\pi} \left\{ \overline{F}(o) + \frac{1}{3}[\overline{F}(D) + \overline{F}(-D)] + \frac{1}{15}[\overline{F}(2D) + \overline{F}(-2D)] + ... \right\}$$

$$G(o) = \frac{4}{D\pi} \left\{ \frac{\overline{F}(o)}{2} - \sum_{n=1}^{N} \frac{\overline{F}(nD)}{(4n^2-1)} \right\}$$

In the final equation about $\overline{F}(o)$, $\overline{F}(nD)$ are directly measured by the collimators and associated detectors.

With reference to FIG. 7, and the previous description, each focal point scan line of each detector I–XII, is divided uniformly into 128 discrete resolution elements, the location of which is the scan field is derived routinely from the mechanism of the gantry scan drive hereinafter more fully described. As a detector passes through the resolution elements of a scan line and uniformly samples the resolution elements, accumulator 810 accumulates counts from the detector photomultipliers for the time of detector travel through each resolution element. For example, for a typical resolution element travel time of 150 milliseconds, the accumulator will receive the counts developed by the detector photomultiplier during 4.8µ second intervals which have an acceptable pulse amplitude as established by a pulse amplitude discriminator circuit in combination with an associated detector. When the counts for a given resolution element have been received by the accumulator 810, this data is transferred to general purpose computer 840 for storage at an address corresponding to the spatial location, i.e. a grid is established in which, for each resolution element in the gird, the corresponding count data representing a quantification of collected counts is stored.

The stored data is then processed by an algorithm, to be discussed in further detail below.

FIGS. 8A and 8B detail the relative positioning and components of just two detectors 400 and 403 which make up the 12 detector array in the twelve camera scanner of the present invention, Each detector consists of a photomultiplier tube (PMT) 407 optically coupled to an 8×5×1 inch NaI scintillating crystal 409 by means of an integrating sphere 405. The crystal 409 is, in turn, attached to the output of a highly focusing lead collimator 411.

FIG. 8A is a view looking down on the 203 mm diameter field of view disk 413 in the transaxial plane, while FIG. 8B is looking at the transaxial plane edge-on. The collimator 411 subtends an angle of about 28° in the transaxial plane as seen in FIG. 15A and 42° in the perpendicular plane as seen in FIG. 8B.

Detector 400 is moved in such a way that its point focus scans the entire near half of the slice in the pattern shown, moving continuously in the x1 direction and making a desired number of equal steps in the y1 direction. The x1 data is accumulated into either 64 or 128 bins. For example, as. As detector 400 makes one full sweep along x1, the number of events detected by PMT 407 is counted and stored (binned) 128 times over 128 equal length intervals. Bins with a large number of counts correspond to detector positions where the detector PSF overlapped areas of high activity.

Detector 403 is shown just 30° from detector 400 and samples the half of the transaxial slice nearest it in its own x2, y2 coordinates which are rotated 30° from x1, y1. In order to avoid collision, the even numbered detectors step in the radially opposite direction from the adjustment odd numbered detectors. In FIG. 8A they are shown in the mid y-step passing position. Since the 12 detectors together collect data over 336° (12×28), ray angles in the transaxial slice are adequately sampled and no circumferential rotation is necessary. The bed is advanced in the axial (z) direction to enable the collimators to scan the next slice.

In order to further improve the resolution of the gamma cameras there are a number of further embodiments provided below which utilize not only an improved gamma camera apparatus, to provide a more precise physical collection of data from the emitting source but also a number of unique application specific algorithms embodied in software for manipulating the acquired data to obtain the most accurate reconstruction and resolved image possible.

Each detector in the known HMX has only one photomultiplier tube. The output of the detector is the sum of all photon detections within its collimator's solid angle. One issue solved by the present invention is, the possible improvement if each detector, like gamma cameras, were position-sensitive and able to keep track of the ray along which each count occurred.

The solution described below is that the main effect of making the detectors position sensitive is to improve the signal-to-noise ratio. This, in turn, improves the fidelity of the reconstruction (which amplifies noise) and, therefore, ultimately the resolution of the reconstructed images. Image resolution depends on the number and arrangement of detectors, an improvement in system performance is achieved by replacing the single-detector collimators of the HMX imager with detector arrays to be described below.

As seen in FIG. 9A, the single 8×5×1 inch NaI crystal of each scanning detector is replaced with two, 4×5×1 inch crystals, c1 and c2, each with its own photomultiplier (PMT). The addition of two crystals and associated photomultipliers improves the signal-to-noise ratio for each scanning detector.

Each detector's PSF spans a rather large (28°×42°) three dimensional bowtie-shaped volume within the FOV. When a gamma-ray is detected, we do not know where within that volume the gamma-ray originated, only the probability distribution of its point-of-origin as given by the normalized PSF. Clearly, if the PSF could be made smaller, the data would provide better locational information. To achieve this, the first embodiment is to replace the single 8×5×1 inches NaI crystal of each detector with two 4×5×1 inches crystals, labeled c1 and c2 in FIG. 9A, and provide each with its own photomultiplier. This divides the PSF in half and increases the number of data values by a factor of two. Now, when a gamma-ray is detected, we will know from which half of the single-detector PSF it originated.

Consider a single conical hole bored into a block of lead Pb of thickness L as shown in FIG. 10, tapered at an angle g and directed along z. The origin 0 of the coordinate system is taken to be the apex of the cone. Clearly the projection of the circular entrance aperture 501 onto the exit plane 503 as seen from the origin O coincides exactly with the circular exit aperture. All photons entering from below exit through the top. For an off-axis point OA on the focal plane the entrance aperture projects on to the exit plane again as a circle of the same radius as before but displaced by an amount determined by the distance of the point form the origin scaled by L/F. Only those photons which intersect the overlapping area of the two circles will get through (why is this important?). The solid angle associated with this area is, for small g, $$\Omega(x, y, 0) = \frac{1}{(L+F)^2} \int\int_{exit\ plane} dx'\,dy'\,\text{circ}\left(\frac{x'}{R'}, \frac{y'}{R}\right)$$

$$\text{circ}\frac{x' + (L/F)x}{R}, \frac{y' + (L/F)y}{R}$$

where the radius R appearing in the circ functions is $$\ell = (L+F)\gamma$$

On planes other than the focal plane, the magnification factor L/F and the radius R in the argument of the second circ function need to be modified. The effect of this is to broaden W(x,y,z) for z<0 (far field) and narrow it for z>0 (near field). However, by conservation fo photons, the integrated solid angle on any plane remains the same. To simplify our analysis, we will assume that W(x,y,z) is independent of z and is given by the expression for W(x,y,0) above. This is not unreasonable since in practice as much activity is scanned by the near field as by the far field. In any case, the exact form of W(x,y) is not important to the purpose fo this section. What is important is the linear dependence of the width W(x,y) on γ.

By superposition, the total clear solid angle through a multi-hole collimator as seen by an emitter at r is given by the sum over holes.)

$$\Omega(r) = \sum_i \Omega_i(r)$$

If the emitter is producing n photons per unit time, the means count rate will be n W(r)4p. When a density of emitters r(r) is scanned by such a collimator, the expected number of observed photons per unit scan volume is given by the convolution.

$$\mu(r) = \int_{emitters} d^3 r' \left(\frac{T}{V}\right) \frac{\Omega(r-r')}{4\pi} v p(r')$$

where T/V is the scan time per unit volume, In k-space, this becomes $$\mu(k) = \left(\frac{T}{V}\right) \frac{\Omega(k)}{4\pi} v p(k)$$

where m(k), W(k) and r(k) are the Fourier Transforms of m(r), W(r) and r(r). Note that m(k) is dimensionless and is equal the total number of expected counts at the spatial frequency k.

We will now evaluate W(k) by performing the sum over holes $$\Omega(k) = \sum_i \Omega_i(k)$$

For our single conical hole directed along z as previously described, we find with the help of the convolution theorem that in cylindrical coordinates $$\Omega(k,\phi,\zeta) = \frac{(\pi R^2)^2}{(F+L)^2} Airy\left(\frac{F(F+L)}{L}\gamma k\right) 2\pi \delta(\zeta)$$

where d is the Dirac delta function and $Airy(x)=(2J_1(x)/x)^2$ in which $J_1$ is the first order Bessel function. For a hole directed along an arbitrary direction $\hat{\eta}$ we have merely to rotate the above expression by replacing d(x) with $\delta(\hat{\eta}\cdot k)$ and interpret k as the radial coordinate in a spherical system. This is an important result. It says that the spatial frequency response of a collimator consisting of a number of holes all focused on a single point may be constructed by the superposition of a "bundle" of planes whose normals point in the directions of the holes.

To carry this out, let $\hat{\eta}=(\sin \theta' \cos \phi', \sin \theta' \sin \phi', \cos \theta')$ and $k=k(\sin \theta \cos \phi, \sin \theta \sin \phi, \cos \theta)$ then $\delta(\hat{\eta}\cdot k)=\delta(\sin \theta \sin \theta' \cos(\phi-\phi')+\cos \theta \cos \theta')/k$ $$\frac{\delta(\phi-\phi'-\phi_r)+\delta(\phi-\phi'+\phi_r)}{k\sqrt{\sin^2\theta+\cos^2\theta'}}$$

where $\pm\phi_r$ are the values of $\phi-\phi'$ for which $\sin \theta \sin \theta' \cos(\phi-\phi')+\cos \theta \cos \theta'$ vanishes. Note that for some combinations of $\theta$ and $\theta'$ no roots exist. To simplify the calculation, we will only consider evaluating W(k) on the transaxial plane $\theta=\pi/2$ an the axial line $\theta=0$.

The HMX scanner uses 12 collimators consisting of point focused conical holes bounded in angle by $(\pi/6)j-\pi/12 \leq \phi'_j \leq (\pi/6)j+\pi/12$ and $(\pi/6)j-\pi/12 \leq \phi'_j \leq (\pi/6)j\pi/12$ where $\alpha=240°$ and j indexes the collimators. Changing the sum over holes to an integral over collimator solid angle yields $$\Omega(k) = \frac{(\pi R^2)^2}{(F+L)^2} Airy\left(\frac{F(F+L)}{L}\gamma k\right) 2\pi$$

$$\int d\theta' \sin\theta' \int d\phi' \left(\frac{dn}{d\Omega}\right) \frac{\delta(\phi-\phi'-\phi_r)+^{\frac{\pi}{2}}\delta(\phi-\phi'+\phi_r)}{k\sqrt{\sin^2\theta+\cos^2\theta'}} + \alpha \frac{\pi}{2} - \alpha$$

where $dn/d\Omega$ is the number of holes per unit solid angle. For a maximally bored collimator this is the reciprocal of the solid angle per hole $1/\pi\lambda^2$. On the transaxial plane the square root in the denominator becomes $\sin \theta'$ and $\phi_r=\pi/2$. The only region of non-vanishing $\Omega$ are the 30° wedges ±90° from the orientation of the collimator $$\phi' + \frac{\pi}{2} - \frac{\pi}{12} \leq \phi \leq \phi' + \frac{\pi}{2} + \frac{\pi}{12} \text{ and}$$

$$\phi' - \frac{\pi}{2} - \frac{\pi}{12} \leq \phi \leq \phi' - \frac{\pi}{2} + \frac{\pi}{12}$$

on which $$\Omega(k) = \frac{(\pi R^2)^2}{(F+L)^2} Airy\left(\frac{F(F+L)}{L}\gamma k\right) \frac{4\alpha}{\gamma^2 k}$$

On the axial line we find $$\Omega(k) = \frac{(\pi R^2)^2}{(F+L)^2} Airy\left(\frac{F(F+L)}{L}\gamma k\right) \frac{\pi/12}{\gamma^2 k}$$

for every detector with all contribution due to the equatorial belt of holes at $\theta'=\pi/2$.

The ability to resolve a feature in the reconstructed image is determined by the largest value of k for which the signal power of the feature remains above the noise power. It is easy to show that noise power in k-space for a given detector is independent of k (white) and, by the nature of Poisson statistics, is equal to the total number of counts N accumulated by the detector over the whole scan.

Two distinct situations are encountered in practice: the imaging of blood flow agents and the imaging of blood flow agents and the imaging of site specific agents. Blood flow agents are taken up globally producing a large noise level which limits the detectability of low-level localized features. Site-specific agents do not produce much noise power but required high bandwidth to resolve. To see what improvements can be made in these situations, we set signal power $|\mu(k)|^2$ to N where $p|(k)|^2$ is the power spectrum of the feature to be resolved $$|\mu(k)|^2 = \left(\frac{T}{V}\right)^2 \left(\frac{\Omega(k)}{4\pi}\right)^2 v^2 |p(k)|^2 = N$$

and apply some simple scaling arguments.

According to the expressions for $\Omega(k)$ on the previous page, we see that signal power depends on k through the two factors, $1/k^2$ and $Airy^2((F(F+L)/L)\gamma k)$. For small k, the first factor governs signal power whereas for k approaching the geometrical limit, the second factor dominates. Generally speaking, in the case of imaging blood-flow agents, we are often bandlimited by the $1/k^2$ factor. In this situation, if the above equation is balanced at a given value of k then decreasing N to say N' will move the crossover point from k to $\sqrt{(N'/N)}\gamma$ since the signal power goes as $\gamma^4$ whereas the nosie power is proportional to $\gamma^2$. According to the argument of the Airy function, this provides an equal measure of increased geometric resolution.

By placing two detectors side-by-side behind each of the twelve HMX's collimators, will effectively create 24 detectors each spanning a unique 15° of asimuthal angle and hence sampling a unique 15° of azimuthal angle in k-space. There will be no loss in signal power, just a clean division between which detector samples which angles. Because the total counts in these smaller detectors is half previous values, the benefits described above are achieved. In going to a 3×2 array of detectors, we create the same situation regarding the sampling of the axial direction and will be able to take advantage of the 3 times reduction in noise power. Other directions in k-space should benefit equally well. Larger arrays will provide greater benefit but may ultimately be limited by scattering and the breakdown in the assumption that each hole provides a perfectly thin plane of sensitivity.

In a still further embodiment, not shown, the single NaI crystal may be divided into three parts, each section measuring 8/3×5×1 inches and having an individual photomultiplier tube coupled to it.

Using a plurality of photomultipliers, the detector may send the individual signals produced by each of the photomultipliers on to the computer for treatment as separate data or conversely it may sum the signals so that they appear to the computer as data from a standard large single detector.

Returning now to FIGS. 9B and 9C, a still further embodiment of the detector consists of a 2×3 array of six individual NaI detector assemblies c1–c6, including photomultiplier tubes. Each crystal is 68 mm in the axial direction and 63 mm in the transverse direction. Another embodiment shown in FIG. 16C utilizes a 3×4 array, each crystal, c1–c12, being 51 mm in the radial direction and 42 mm in the axial direction. The crystals of the arrays are approximately 19 mm thick, compared to the known crystals being about 25.4 mm thick. These arrays are currently sized to fit with the current 127×203 mm (5×8 in) envelop of the presently designed machines, although it is to be appreciated that different size crystals could be incorporated with machines having different size envelopes. The important result of the arrayed crystals is the improved energy resolution obtained for data generation.

Larger arrays are possible, however eventually the information provided by one array element will become redundant with its neighboring elements. From a practical point of view, the number of usable elements is limited by cost and the ability to handle the increased data rates and processing load.

A variation of this scheme is to leave the 8×5×1 inch NaI crystal in one piece and look at the signal crystal with an array of photomultipliers to detect the scintillation light rather than a single detector. By comparing the outputs of each photomultiplier, the collimator hole in which the interdependence of slice data is due mostly to the axial extent of the PSF and, to a lesser extent, axial correlations in the distribution of radioactivity in the head. The new algorithm, to be discussed in further detail below, obtains the distribution of radioactivity which is most probable given the data and assumed prior information on the statistics of that distribution. This solution is known as a maximum a-posteriori (MAP) reconstruction. The previous reconstruction used a filter and back project technique which could not model the counts as Poisson distributed random variables is correct but instead modeled them as Gaussian distributed with zero mean and a stationary variance.

In a yet further embodiment, in combination with the above described single or multiple NaI crystals, the system resolution can be further improved by replacing the present 800-hole collimator with a 1200-hole collimator. Manufacturing tolerances may impose a physical limitation on how small each rectangular hole in the collimator can be made, however, another alternative is to leave the hole size constant and make the collimator longer.

Another embodiment combines (stacks) collimators in series as seen schematically in FIG. 11. Each collimator would have the same focal point P in space.

Given the above described improvements in the acquisition of accurate data from the emitting source, the manipulation of this data to account for error, absorption and other interference in the physical data collection by the following method of reconstruction will now be described.

In order to provide a usable, viewable 2 dimensional or 3 dimensional image accurately reflecting the scanned section of the source, namely a body organ, it is necessary to provide a method for accurately reconstructing the accumulated digital data stored in the host computer into a viewable image. As is known, the emitted gamma rays from the source, for example the brain, induce a gamma ray scintillation at the NaI crystal causing the release of photons which are "counted" by the photomultiplier tube. The digital signals of the "count" are then stored in the host computer.

It is important to reconstruct as accurately as possible an image optimally reflecting the true emission of the energetic gamma rays from the source, therefore the error inherent in the collection of the count must be eliminated to the extent possible. Because of the highly unique scanning motion designed to cause the gamma lens foci to uniformly sample the head as is described above, the optimum reconstruction of images from the data collected requires not only an accurate actual scan of the source but a specific simulation of this unique scanning motion for error elimination purposes to be described in further detail below.

Turning now to FIGS. 12A, and 12B, FIG. 12A shows a transaxial brain image using the below described 3-dimensional reconstruction. FIG. 12B is an image of a Data Spectrum phantom using the standard 2D reconstruction. The last pie section to be clearly resolved consists of an array of 6.4 mm cylinders. The fainter spots located midway between the pie sections are due to some radioactivity leakage along the six threaded rods holding the phantom together.

Over the years scans on many animals were made with the HMX using βCIT as the injected receptor agent to image the functioning of the caudate nucleus. Old "raw" scan data from the African green monkey model was utilized to perform a new, fully 3-dimensional reconstruction.

Observing FIGS. 13A and 13B, a profile through the radioactive marker on the nose is shown at FIG. 19A and a horizontal profile through the head of the caudate nuclei at FIG. 13B. Not only are the left and right caudate completely separated in this small animal but the putamen is resolved from the caudate.

Therefore, at least in the case of receptor imaging with its relatively high image contrast, the resolution of the HMX using the new fully 3D reconstruction is now 3–4 mm. And more preferably a resolution of 2–3 mm is obtainable by using position sensitive detectors discussed herein.

As shown in FIG. 14, the system consists of two parts: (1) the host computer 700 and (2) the scanner 703, and its associated detectors and collimators as previously discussed. The scanner 703 also includes its own microprocessors and code which control the radial movement of and relative timing between the detectors, performs data acquisition via the above discussed multiple arrays of photomultiplier tubes, and transmits the data via serial cable 705 to the host computer 700. Certain physical attributes of the scanner 703 are difficult to readily improve upon due to manufacturing and practicality purposes. Some of these attributes which improve the data acquisition and the image reconstruction, can, however be enhanced utilizing the following methods of reconstruction as implemented for example by a computer program on the host computer 700 and described in further detail below.

Turning now to FIG. 15 the host computer 700 initiates a scan by sending certain setup parameters at step 710 (for example, the number of slices) to the scanner 703 and instructing the scanner to start at step 711. During the scan, acquired data is sent to the host computer in a continuous stream and compiled at step 713 on its hard disk. The operator may instruct the computer to perform a 2-dimensional, slice-by-slice reconstruction at step 715 while the scan is taking place for the purpose of visually monitoring at step 717 the progress of the scan on the display device 707. Upon completion of acquiring a complete data set for each slice and reconstructing this data into a complete visually observable 2 dimensional slice at step 718, a full 3-dimensional reconstruction is performed at step 719 combining the individual slices into a 3 dimensional model which is visually and statistically superior in all aspects, to the 2D reconstruction.

Reconstruction

The purpose of the reconstruction, whether 2-dimensional or 3-dimensional, is to determine, given the acquired data, the most likely three dimensional distribution of radioactivity concentration present in the head at the time of scanning. Observing FIG. 16, the maximum a-posterior (MAP) algorithm described is incorporated in both the 2D and 3D reconstructions and is uniquely applicable to the above described system. This algorithm involves an iterative process, which at each iteration, "moves" the reconstructing distribution of radioactivity from an initial starting point to the final solution. The direction of the move at step n is determined from a comparison of a computer simulated scan of the solution at step n with the actual scan data. The steps involved are as follows:

1. Load scan data into memory at step 730.
2. Initiate the solution to zero at step 731, i.e. guess the distribution of radioactivity in the head (an initial guess may start such a distribution at zero).
3. Perform a simulated scan of that distribution at step 733.
4. Compare, at step 735, the simulated scan data collected at step 733 with the real data from the actual scan data and modify the distribution of radioactivity at step 739, so that on the next pass, the simulated scan data will better match the real data. (Again, how the correction is made is specific to our scanner although the math one goes through to determine this for any scanner is well known).
5. Determine at step 741 if the solution has changed from the last iteration, i.e. whether actual scan data and simulated scan data from step 733 agree within the known statistical noise of the real data, if yes, then the reconstruction is complete, if no then, steps 735-741 are reiterated until the simulated data and real data agree to within the known statistical noise of the real data.

Scan Simulation

The goal of the simulation is to model as accurately as possible the propagation of gamma-rays through the tissues of the head a well as the efficiencies, PSFs and motions of the detectors. Clearly, the better the simulation, the better will be the agreement between the reconstructed source distribution and the true source distribution when the simulated data converges to the real data.

FIG. 17, outlines the simulation procedure. The PSF is generated at step 750 at the start of each reconstruction, computing, for every source location in the field-of-view, the total solid angle of acceptance allowed by the collimator. This is a straight forward geometry problem, involving the projection of the rectangular holes on the entrance plane of the collimator onto the collimator's exit plane, taking the intersection of the projected rectangular exit-plane holes, multiplying by a cosine/$r^2$ factor and summing over all holes. As this is well known in the art no further discussion is provided herein.

As described earlier, in the actual data collection process there are 12 detectors whose foci simultaneously raster scan the head along three orthogonal axes. Mathematically, scanning involves the convolution of the detector PSFs with the distribution of radioactivity. This is implemented on the computer using the Fast Fourier Transform (FFT) method. By utilizing both real and imaginary components of the FT arrays, we perform two fo the 12 convolutions with each FFT pair requiring six FFT pairs all together to complete the 12 convolutions.

Before a convolution is performed, an attenuation map 751 is applied to the source on a point by point basis to simulate the loss of gamma rays due to absorption in the head as they make their way toward the detector. The twelve 3D attenuation maps are pre-computed at step 753 at the start of a reconstruction using a set of ellipses in step 755, one per slice, which describe the boundary between head and air and assuming absorption is constant within the head and zero outside. For each cell location within a slice and for each detector, attenuation is obtained by averaging $\exp(-\mu s)$ over the detector's 30° angular field-of-view where s is the distance a gamma ray traverses through the region inside the slice's ellipse on it way to the detector and μ is the tissue attenuation coefficient. Ellipses are computed from a prior 2D reconstructions at step 757 and are user adjustable in the event the computed ellipses are not deemed satisfactory.

A better strategy for simulating absorption is to acquire two sets of data during the actual scan where the second set contains only counts of scattered gamma rays and use a reconstruction of that data to set the distribution of absorbers in the simulation assuming equivalence of scatterers and absorbers.

Turning now to FIG. 18, the convolution algorithm is:

FOR i=1 TO 6

1. At step 760 apply the attenuation map corresponding to detector i to source.
2. At step 761 rotate the attenuated source by −30i degrees.
3. At step 763 sub-sample the rotated, attenuated source along the longitudinal direction of the collimator by a factor of 4 and at step 764 put into the real part of a 3D complex array. (Sub sampling is not required but speeds things up by a factor of 4 and still maintains Nyquist sampling rates).
4. Apply the attenuation map for detector i+6 to source at step 765.
5. Rotate the attenuated source by −30i+180 degrees at step 767.
6. At step 769 sub-sample the rotated, attenuated source along the longitudinal direction fo the collimator by a factor of 4 and put into the imaginary part of the same 3D complex array.
7. At step 770 perform a 3D Fast Fourier Transform (FFT) on the complex array.
8. At step 771 multiply by the PSF (This is pre-computed at the start of the reconstruction and is referred to as the modulation transfer function (MTF).
9. At step 773 Inverse FFT.
10. Extract real and imaginary parts and set aside at step 775. LOOP.

The next step is to apply any known systematic errors inherent in the actual scan to the simulated scan. Currently we consider errors in the locations of the detectors and variation in the efficiencies of the detectors. These are determined from calibration protocols typically done once a day. Offsets are determined form a scan of a line of activity placed on axis and in the center of the scanner. Efficiencies are determined from a scan of a large uniform "flood" source which fills the field-of-view of the scanner.

Source Correction

After adjusting our 12 sets of 3D simulated scans to correspond as best we can to actual data, we subtract one from the other. What remains is what we would like to get rid of in the next iteration of the reconstruction. To convert this residual error into a source correction, we perform the steps 1 the 10 steps listed above but in reverse order using the complex conjugate of the MTF, over-sampling instead of sub-sampling and counter rotations. The 12 distributions generated in this manner are summed to form a single 3D distribution whose elements have a one-to-one correspondence with the elements of the source.

Additional information regarding the source distribution is now incorporated into the correction. First, we compute the Laplacian of the source by subtracting from each source element a weighted average of its 26 nearest neighbors, scale this by a user selectable amount, then subtract this 3D distribution from the source correction computed above. The purpose of this is to incorporate into the final solution a prior knowledge of spatial correlation (smoothness). We also provide for adaptive smoothing such that regions of low activity are smoothed more than regions of high activity. Furthermore, when the correction is finally applied, source elements which become negative are set to zero as negative radioactivity is physically not allowed.

What is claimed is:

1. A method of digitally constructing and visually displaying brain function activity comprising the steps of:
    injecting a radioactive isotope into a source brain to facilitate the emission of gamma radiation from the source brain;
    scanning the gamma radiation emitted along a first plane of the brain and storing a respective first distribution of collected counts of radioactivity as actual scan data in an electronic storage device;
    digitally reconstructing a brain function image from a comparison between the actual scan data of the brain source and a theoretical scan of the brain source; and
    visually displaying the brain function image as a representation of brain function activity;
    wherein the digitally reconstructing step further comprises the steps of estimating a second distribution of radioactivity in the source brain and performing a simulated scan of the estimated second distribution to obtain the theoretical scan; and
    wherein the step of the reiterated comparison between theoretical and actual scan data further comprises the steps of comparing the theoretical scan with the actual scan data and modifying the estimated second distribution to obtain a solution gamma radiation distribution which more closely match the actual scan data; and
    further comprising the step of determining whether the solution compares to the actual scan data within a desired statistical noise.

2. The method of digitally constructing and visually displaying brain function activity as set forth in claim 1 wherein when the solution fails to compare to the actual scan data within the desired statistical noise, the method further comprises the step of modifying the solution with the actual scan data and obtaining a modified solution for comparison with the actual scan data.

3. The method of digitally constructing and visually displaying brain function activity as set forth in claim 1 wherein when the modified solution compares to the actual scan data within the desired statistical noise, a final completed visual image is produced which displays the solution gamma radiation distribution at a desired resolution.

4. A method of digitally constructing and visually displaying brain function activity comprising the steps of:
    injecting a radioactive isotope into a source brain to facilitate the emission of gamma radiation from the source brain;
    scanning the gamma radiation emitted along a first plane of the brain and storing a respective first distribution of collected counts of radioactivity as actual scan data in an electronic storage device;
    digitally reconstructing a brain function image from a comparison between the actual scan data of the brain source and a theoretical scan of the brain source; and
    visually displaying the brain function image as a representation of brain function activity;
    further comprising the steps of, before digitally reconstructing the brain function image, repeating the scanning of the gamma radiation emitted along a second through an $n^{th}$ plane of the brain and storing the respective second through $n^{th}$ distributions of collected counts of radioactivity as actual scan data in the electronic storage device.

5. A method of digitally constructing and visually displaying brain function activity using a brain function imaging apparatus for scanning, mapping and visually displaying functional brain activity, the brain function imaging apparatus comprising a gantry supporting a plurality of gamma ray detectors, each of said plurality of detectors having a converging collimator for collecting gamma rays emitted from a radioactive source in the brain, at least a scintillation crystal is attached to an end of each collimator for converting the emitted gamma rays from the brain into photons of light and at least a photomultiplier tube is coupled to each scintillation crystal for producing a count of emitted gamma rays, a data processor for digitally compiling the count of gamma radiation and visually reconstructing a digital image reflecting the emitted gamma radiation on a display device, each of the plurality of converging collimators is a short focus collimator having a focal point within the scanned radioactive source, the method comprising the steps of:
 injecting a radioactive isotope into a source brain to facilitate the emission of gamma radiation from the source brain;
 scanning the emitted gamma radiation with the plurality of gamma ray detectors, and storing a first distribution of collected counts of radioactivity as actual scan data in the data processor;
 repeating the scanning of the gamma radiation emitted along a sequentially adjacent first through $n^{th}$ plane of the brain and storing a respective first through $n^{th}$ distributions of collected counts of radioactivity as actual scan data in the electronic storage device;
 digitally reconstructing the brain function from a reiterated comparison between the actual scan data from the sequentially adjacent first through $n^{th}$ plane of the brain source and a theoretical scan of each adjacent plane of the brain source; and
 visually displaying the digital reconstruction of each adjacent first through $n^{th}$ plane of the brain as a 3-dimensional image of the brain function activity on the display device;
 wherein the digitally reconstructing step further comprises the steps of estimating a second distribution of radioactivity in the source brain and performing a simulated scan of the estimated second distribution to obtain the theoretical scan;
 further comprising the steps of comparing the theoretical scan with the actual scan data and modifying the estimated second distribution to obtain a solution which more closely match the actual scan data; and
 further comprising the step of determining whether the solution compares to the actual scan data within a desired statistical noise.

6. The method of digitally constructing and visually displaying brain function activity as set forth in claim 5 wherein when the solution fails to compare to the actual scan data within the desired statistical noise the method further comprises the step of modifying the solution with the actual scan data and obtaining a modified solution for comparison with the actual scan data.

7. The method of digitally constructing and visually displaying brain function activity as set forth in claim 5 wherein when the modified solution compares to the actual scan data within the desired statistical noise, a final completed output is produced which visually displays the gamma radiation distribution from the source brain on the display device at a desired resolution.

8. A method of digitally constructing and visually displaying brain function activity using a brain function imaging apparatus for scanning, mapping and visually displaying functional brain activity, the brain function imaging apparatus comprising a gantry supporting a plurality of gamma ray detectors, each of said plurality of detectors having a converging collimator for collecting gamma rays emitted from a radioactive source in the brain, at least a scintillation crystal is attached to an end of each collimator for converting the emitted gamma rays from the brain into photons of light and at least a photomultiplier tube is coupled to each scintillation crystal for producing a count of emitted gamma rays, a data processor for digitally compiling the count of gamma radiation and visually reconstructing a digital image reflecting the emitted gamma radiation on a display device, each of the plurality of converging collimators is a short focus collimator having a focal point within the scanned radioactive source, the method comprising the steps of:
 injecting a radioactive isotope into a source brain to facilitate the emission of gamma radiation from the source brain;
 scanning the emitted gamma radiation with the plurality of gamma gamma ray detectors, and storing a first distribution of collected counts of radioactivity as actual scan data in the data processor;
 repeating the scanning of the gamma radiation emitted along a sequentially adjacent first through $n^{th}$ plane of the brain and storing a respective first through $n^{th}$ distributions of collected counts of radioactivity as actual scan data in the electronic storage device;
 digitally reconstructing the brain function from a reiterated comparison between the actual scan data from the sequentially adjacent first through $n^{th}$ plane of the brain source and a theoretical scan of each adjacent plane of the brain source; and
 visually displaying the digital reconstruction of each adjacent first through n plane of the brain as a 3-dimensional image of the brain function activity on the display device;
 wherein each detector is provided with 3 separate scintillation crystals each crystal having an associated photomultiplier tube for providing three channels of input to the data processor from each detector.

9. A method of digitally constructing and visually displaying brain function activity using a brain function imaging apparatus for scanning, mapping and visually displaying functional brain activity, the brain function imaging apparatus comprising a gantry supporting a plurality of gamma ray detectors, each of said plurality of detectors having a converging collimator for collecting gamma rays emitted from a radioactive source in the brain, at least a scintillation crystal is attached to an end of each collimator for converting the emitted gamma rays from the brain into photons of light and at least a photomultiplier tube is coupled to each scintillation crystal for producing a count of emitted gamma rays, a data processor for digitally compiling the count of gamma radiation and visually reconstructing a digital image reflecting the emitted gamma radiation on a display device, each of the plurality of converging collimators is a short focus collimator having a focal point within the scanned radioactive source, the method comprising the steps of:
 injecting a radioactive isotope into a source brain to facilitate the emission of gamma radiation from the source brain;

scanning the emitted gamma radiation with the plurality of gamma ray detectors, and storing a first distribution of collected counts of radioactivity as actual scan data in the data processor;

repeating the scanning of the gamma radiation emitted along a sequentially adjacent first through $n^{th}$ plane of the brain and storing a respective first through $n^{th}$ distributions of collected counts of radioactivity as actual scan data in the electronic storage device;

digitally reconstructing the brain function from a reiterated comparison between $n^{th}$ actual scan data from the sequentially adjacent first through $n^{th}$ plane of the brain source and a theoretical scan of each adjacent plane of the brain source; and visually displaying the digital reconstruction of each adjacent first through $n^{th}$ plane of the brain as a 3-dimensional image of the brain function activity on the display device;

wherein each converging collimator of each detector comprises a plurality of stacked collimators.

* * * * *